US011065100B2

(12) United States Patent
Parodi et al.

(10) Patent No.: US 11,065,100 B2
(45) Date of Patent: Jul. 20, 2021

(54) VASCULAR REPAIR DEVICES AND METHODS OF USE

(71) Applicant: Bolton Medical, Inc., Sunrise, FL (US)

(72) Inventors: Juan Carlos Parodi, Provincia de Buenos Aires (AR); Samuel Arbefeuille, Sunrise, FL (US); John C. Canning, Sunrise, FL (US); Fletcher Christian, Sunrise, FL (US); Scott Lyle Rush, Sunrise, FL (US); Bryan White, Sunrise, FL (US); Eduardo Alejandro Garcia, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 34 days.

(21) Appl. No.: 16/692,845

(22) Filed: Nov. 22, 2019

(65) Prior Publication Data

US 2020/0085560 A1 Mar. 19, 2020

Related U.S. Application Data

(62) Division of application No. 14/861,479, filed on Sep. 22, 2015, now Pat. No. 10,524,893.

(Continued)

(51) Int. Cl.
*A61F 2/06* (2013.01)
*A61F 2/07* (2013.01)
(Continued)

(52) U.S. Cl.
CPC ............. *A61F 2/07* (2013.01); *A61F 2/848* (2013.01); *A61F 2/89* (2013.01); *A61F 2/06* (2013.01);
(Continued)

(58) Field of Classification Search
CPC ...... A61F 2/06; A61F 2/07; A61F 2/89; A61F 2/852; A61F 2/856; A61F 2/848; A61F 2002/061; A61F 2002/067
See application file for complete search history.

(56) References Cited

U.S. PATENT DOCUMENTS 4,501,263 A 2/1985 Harbuck
5,123,917 A 6/1992 Lee
(Continued)

FOREIGN PATENT DOCUMENTS

CN 201230914 Y 5/2009
CN 101601618 A 12/2009
(Continued)

OTHER PUBLICATIONS

"Bolton Medical Thoracic Branch Graft Case Presentation," Charing Cross Symposium Annual Meeting, London, Apr. 8-12, 2011.
(Continued)

*Primary Examiner* — Dinah Baria
(74) *Attorney, Agent, or Firm* — Foley Hoag LLP

(57) ABSTRACT

A vascular repair device assembly includes a main prostheses, first internal prostheses, an optional second internal prostheses, and at least two sub-prostheses. Methods for delivering vascular repair devices include delivering a vascular repair device through a blood vessel to the aneurysm site, aligning a proximal open end of a main prosthesis cranially to the site of the aneurysm patient and directing a distal end of at least one additional one vascular repair device through a proximal end of at least a first internal lumen, and aligning the proximal end of the additional vascular repair device into a distal end of the at least one sub-prosthesis.

5 Claims, 23 Drawing Sheets

Related U.S. Application Data

(60) Provisional application No. 62/054,064, filed on Sep. 23, 2014.

(51) Int. Cl.
*A61F 2/848* (2013.01)
*A61F 2/89* (2013.01)
*A61F 2/856* (2013.01)
*A61F 2/852* (2013.01)

(52) U.S. Cl.
CPC ............... *A61F 2/852* (2013.01); *A61F 2/856* (2013.01); *A61F 2002/061* (2013.01); *A61F 2002/065* (2013.01); *A61F 2002/067* (2013.01); *A61F 2002/075* (2013.01); *A61F 2002/8483* (2013.01); *A61F 2220/0016* (2013.01); *A61F 2220/0075* (2013.01); *A61F 2250/006* (2013.01); *A61F 2250/0039* (2013.01)

(56) References Cited

U.S. PATENT DOCUMENTS

| | | |
|---|---|---|
| 5,231,989 A | 8/1993 | Middleman et al. |
| 5,507,769 A | 4/1996 | Marin et al. |
| 5,575,817 A | 11/1996 | Martin |
| 5,683,449 A | 11/1997 | Marcade |
| 5,755,772 A | 5/1998 | Evans et al. |
| 5,843,160 A | 12/1998 | Rhodes |
| 5,855,598 A | 1/1999 | Pinchuk |
| 5,984,955 A | 11/1999 | Wisselink |
| 6,059,824 A | 5/2000 | Taheri |
| 6,171,334 B1 | 1/2001 | Cox |
| 6,187,033 B1 | 2/2001 | Schmitt et al. |
| 6,210,429 B1 | 4/2001 | Vardi et al. |
| 6,280,464 B1 | 8/2001 | Hayashi |
| 6,306,141 B1 | 10/2001 | Jervis |
| 6,344,056 B1 | 2/2002 | Dehdashtian |
| 6,395,018 B1 | 5/2002 | Castaneda |
| 6,585,756 B1 | 7/2003 | Strecker |
| 6,595,963 B1 | 7/2003 | Barbut |
| 6,645,242 B1 | 11/2003 | Quinn |
| 6,676,699 B2 | 1/2004 | Shiu |
| 6,814,752 B1 | 11/2004 | Chuter |
| 7,144,421 B2 | 12/2006 | Carpenter et al. |
| 7,294,147 B2 | 11/2007 | Hartley |
| 7,407,509 B2 | 8/2008 | Greenberg et al. |
| 7,435,253 B1 | 10/2008 | Hartley et al. |
| 7,438,721 B2 | 10/2008 | Doig et al. |
| 7,537,606 B2 | 5/2009 | Hartley et al. |
| 7,550,004 B2 | 6/2009 | Bahler et al. |
| 7,641,646 B2 | 1/2010 | Kennedy, II |
| 7,731,744 B1 | 6/2010 | Cox |
| 7,763,063 B2 | 7/2010 | Arbefeuille et al. |
| 7,828,837 B2 | 11/2010 | Khoury |
| 7,854,758 B2 | 12/2010 | Taheri |
| 7,914,572 B2 | 3/2011 | Hartley et al. |
| 8,007,605 B2 | 8/2011 | Arbefeuille et al. |
| 8,021,419 B2 | 9/2011 | Hartley et al. |
| 8,048,140 B2 | 11/2011 | Purdy |
| 8,062,345 B2 | 11/2011 | Ouellette et al. |
| 8,062,349 B2 | 11/2011 | Moore et al. |
| 8,070,790 B2 | 12/2011 | Berra et al. |
| 8,092,511 B2 | 1/2012 | Chuter |
| 8,167,930 B2 | 5/2012 | Allen et al. |
| 8,172,895 B2 | 5/2012 | Anderson et al. |
| 8,267,988 B2 | 9/2012 | Hamer et al. |
| 8,292,943 B2 | 10/2012 | Berra et al. |
| 8,333,800 B2 | 12/2012 | Bruszewski et al. |
| 8,337,546 B2 | 12/2012 | Bruszewski |
| 8,394,136 B2 | 3/2013 | Hartley et al. |
| 8,474,120 B2 | 7/2013 | Hagaman et al. |
| 8,500,792 B2 | 8/2013 | Berra |
| 8,545,549 B2 | 10/2013 | Hartley et al. |
| 8,556,961 B2 | 10/2013 | Quinn |
| 8,574,284 B2 | 11/2013 | Roeder et al. |
| 8,663,310 B2 | 3/2014 | Greenberg et al. |
| 8,672,993 B2 | 3/2014 | Chuter et al. |
| 8,728,145 B2 | 5/2014 | Chuter et al. |
| 8,740,966 B2 | 6/2014 | Brocker et al. |
| 8,753,386 B2 | 6/2014 | Shaw |
| 8,795,349 B2 | 8/2014 | Huser et al. |
| 8,870,939 B2 | 10/2014 | Roeder et al. |
| 8,940,040 B2 | 1/2015 | Shahriari |
| 8,945,202 B2 | 2/2015 | Mayberry et al. |
| 8,945,205 B2 | 2/2015 | Greenberg |
| 8,992,593 B2 | 3/2015 | Chuter et al. |
| 8,998,970 B2 | 4/2015 | Arbefeuille et al. |
| 8,998,971 B1 | 4/2015 | Kelly |
| 9,034,027 B2 | 5/2015 | Ivancev |
| 9,095,456 B2 | 8/2015 | Ivancev et al. |
| 9,101,455 B2 | 8/2015 | Roeder et al. |
| 9,101,506 B2 | 8/2015 | Arbefeuille et al. |
| 9,149,382 B2 | 10/2015 | Greenberg et al. |
| 9,173,755 B2 | 11/2015 | Berra et al. |
| 9,198,786 B2 | 12/2015 | Moore et al. |
| 9,259,336 B2 | 2/2016 | Schaeffer et al. |
| 9,320,631 B2 | 4/2016 | Moore et al. |
| 9,345,595 B2 | 5/2016 | Brocker et al. |
| 9,364,314 B2 | 6/2016 | Berra et al. |
| 9,439,751 B2 | 9/2016 | White et al. |
| 9,463,102 B2 | 10/2016 | Kelly |
| 9,592,112 B2 | 3/2017 | Arbefeuille et al. |
| 9,597,209 B2 | 3/2017 | Khoury |
| 9,649,188 B2 | 5/2017 | Hartley |
| 9,655,712 B2 | 5/2017 | Berra et al. |
| 9,724,187 B2 | 8/2017 | Ivancev et al. |
| 9,877,857 B2 | 1/2018 | Arbefeuille et al. |
| 10,182,930 B2 | 1/2019 | Moore et al. |
| 10,213,291 B2 | 2/2019 | Berra et al. |
| 10,390,932 B2 | 8/2019 | Lostetter |
| 10,524,893 B2 | 1/2020 | Parodi et al. |
| 2002/0013620 A1 | 1/2002 | Kujawski |
| 2002/0052643 A1 | 5/2002 | Wholey et al. |
| 2002/0062133 A1 | 5/2002 | Gilson et al. |
| 2003/0120333 A1 | 6/2003 | Ouriel et al. |
| 2003/0130725 A1 | 7/2003 | DePalma et al. |
| 2003/0204242 A1 | 10/2003 | Zarins et al. |
| 2005/0059923 A1 | 3/2005 | Gamboa |
| 2005/0131518 A1 | 6/2005 | Hartley et al. |
| 2005/0131523 A1 | 6/2005 | Bashiri et al. |
| 2005/0177222 A1 | 8/2005 | Mead |
| 2006/0095118 A1 | 5/2006 | Hartley |
| 2007/0055350 A1 | 3/2007 | Erickson et al. |
| 2007/0106368 A1 | 5/2007 | Vonderwalde |
| 2007/0135818 A1 | 6/2007 | Moore et al. |
| 2007/0168013 A1 | 7/2007 | Douglas |
| 2007/0198078 A1 | 8/2007 | Berra et al. |
| 2008/0091260 A1 | 4/2008 | Pomeranz et al. |
| 2008/0114444 A1 | 5/2008 | Yu |
| 2008/0264102 A1 | 10/2008 | Berra |
| 2009/0048663 A1 | 2/2009 | Greenberg |
| 2009/0125100 A1 | 5/2009 | Mead |
| 2009/0264988 A1 | 10/2009 | Mafi et al. |
| 2009/0319022 A1 | 12/2009 | Hartley et al. |
| 2010/0030255 A1 | 2/2010 | Berra et al. |
| 2010/0057186 A1 | 3/2010 | West et al. |
| 2011/0087318 A1 | 4/2011 | Daugherty et al. |
| 2011/0118821 A1 | 5/2011 | Brocker et al. |
| 2011/0245906 A1 | 10/2011 | DiMatteo et al. |
| 2011/0257731 A1 | 10/2011 | Hartley et al. |
| 2012/0123464 A1 | 5/2012 | Rasmussen et al. |
| 2012/0158121 A1 | 6/2012 | Ivancev et al. |
| 2012/0245672 A1 | 9/2012 | Arbefeuille et al. |
| 2012/0271401 A1 | 10/2012 | Bruszewski et al. |
| 2012/0296414 A1 | 11/2012 | Hartley |
| 2012/0310324 A1 | 12/2012 | Benary et al. |
| 2013/0013053 A1 | 1/2013 | Hartley et al. |
| 2013/0079870 A1 | 3/2013 | Roeder et al. |
| 2013/0197627 A1 | 8/2013 | Jensen et al. |
| 2013/0211506 A1 | 8/2013 | Dake et al. |
| 2013/0268059 A1 | 10/2013 | Hagaman et al. |
| 2013/0282103 A1 | 10/2013 | Madjarov et al. |

(56) References Cited

U.S. PATENT DOCUMENTS

| | | |
|---|---|---|
| 2014/0046428 A1 | 2/2014 | Cragg et al. |
| 2014/0135890 A9 | 5/2014 | Berra |
| 2014/0243952 A1 | 8/2014 | Parodi |
| 2014/0277347 A1 | 9/2014 | Daugherty et al. |
| 2014/0277370 A1 | 9/2014 | Brocker et al. |
| 2014/0277379 A1 | 9/2014 | Vogel et al. |
| 2016/0008178 A1 | 1/2016 | Babic et al. |
| 2016/0184077 A1 | 6/2016 | Choubey et al. |
| 2016/0184078 A1 | 6/2016 | Choubey et al. |
| 2016/0184115 A1 | 6/2016 | Ondersma et al. |
| 2016/0310301 A1 | 10/2016 | Moore et al. |
| 2017/0000600 A1 | 1/2017 | Berra et al. |
| 2017/0007392 A1 | 1/2017 | Louren O et al. |
| 2017/0100232 A1 | 4/2017 | Arbefeuille et al. |
| 2017/0281332 A1 | 10/2017 | Lostetter |
| 2017/0281382 A1 | 10/2017 | Lostetter et al. |
| 2017/0319359 A1 | 11/2017 | Mehta |
| 2017/0325977 A1 | 11/2017 | Sarac et al. |
| 2017/0340433 A1 | 11/2017 | Berra et al. |
| 2017/0340462 A1 | 11/2017 | Lostetter |
| 2018/0071123 A1 | 3/2018 | Arbefeuille et al. |
| 2018/0078394 A1 | 3/2018 | Zimmerman et al. |
| 2018/0206972 A1 | 7/2018 | Arbefeuille et al. |
| 2019/0192324 A1 | 6/2019 | Moore et al. |
| 2020/0085560 A1 | 3/2020 | Parodi et al. |

FOREIGN PATENT DOCUMENTS

| | | |
|---|---|---|
| CN | 102379757 A | 3/2012 |
| CN | 102488575 A | 6/2012 |
| CN | 102641164 A | 8/2012 |
| CN | 103876860 A | 6/2014 |
| CN | 203841852 U | 9/2014 |
| CN | 104287871 A | 1/2015 |
| CN | 102973303 B | 2/2015 |
| CN | 104367400 A | 2/2015 |
| CN | 104546221 A | 4/2015 |
| CN | 105030373 A | 11/2015 |
| EP | 1487380 B1 | 2/2008 |
| EP | 2051663 B1 | 11/2009 |
| EP | 2139429 B1 | 6/2011 |
| EP | 2331013 B1 | 11/2014 |
| WO | WO-2001/032103 A1 | 5/2001 |
| WO | WO-2002/038085 A1 | 5/2002 |
| WO | WO-2006/113501 A1 | 10/2006 |
| WO | WO-2007/123956 A2 | 11/2007 |
| WO | WO-2009/124124 A1 | 10/2009 |
| WO | WO-2013/025727 A1 | 2/2013 |
| WO | WO-2014/149022 A1 | 9/2014 |
| WO | WO-2015/116715 A1 | 8/2015 |
| WO | WO-2015/188775 A1 | 12/2015 |
| WO | WO-2017/218474 A1 | 12/2017 |
| WO | WO-2018/026768 A1 | 2/2018 |
| WO | WO-2018/031632 A1 | 2/2018 |

OTHER PUBLICATIONS

Browne et al., "Endovascular and surgical techniques: A fenestrated covered suprarenal aortic stent," Eur J Vasc Endovasc Surg, 18:445-449 (1999).

Chuter et al., "Development of a branched stent-graft for endovascular repair of aortic arch aneurysms," J Endovasc Ther, 10:940-945 (2003).

Chuter et al., "Modular branched stent graft for endovascular repair of aortic arch aneurysm and dissection," J Vasc Surg, 38:859-863 (2003).

Funovics, "Branched endografts for aortic arch aneurysms—How close are we?," CIRSE 2011 Conference, Munich Germany, Session No. 802.3 (Sep. 10-14, 2011).

Funovics, "TEVAR in the ascending aorta: A new frontier for endografting—preliminary results and technology transfer," Focus Meeting, Bolton Medical Inc., Barcelona, Spain (Oct. 2011).

Inoue et al., "Aortic arch reconstruction by transluminally placed endovascular branched stent graft," Circulation, 100(Suppl II):II-316-II-321 (1999).

Inoue et al., "Clinical endovascular placement of branched graft for type B aortic dissection," J Thorac Cardiovasc Surg, 112:1111-1113 (1996).

Inoue et al., "Transluminal endovascular branched graft placement for a pseudoaneurysm: Reconstruction of the descending thoracic aorta including the celiac axis," J Thorac Cardiovasc Surg, 114:859-861 (1997).

International Preliminary Report on Patentability for International Application No. PCT/US2015/051470 dated Mar. 28, 2017.

International Search Report and Written Opinion for International Application No. PCT/US2015/051470 dated Dec. 4, 2015.

Kinney et al., "Repair of mycotic paravisceral aneurysm with a fenestrated stent-graft," J Endovasc Ther, 7:192-197 (2000).

Lioupis et al., "Treatment of aortic arch aneurysms with a modular transfemoral multibranched stent graft: Initial experience," European Journal of Vascular and Endovascular Surgery, 43:525-532 (2012).

Martinelli, "Partial ascending aorta and total arch reconstruction with bolton medical branched thoracic endograft," Cardiovascular Surgery Meeting, Bologna, Italy (Nov. 14-15, 2011).

Ouriel et al., "Branched device to preserve hypogastric arterial flow with thoracoabdominal aneurysm repair," J Vasc Surg, 37:481 (2003).

Simring et al., "Total endovascular repair of the arch: Branched endografting makes it easy," Tecnicas Endovasculares, 14(1):3712-3716 (2011).

Wisselink et al., "Endoluminal Repair of Aneurysms Containing Ostia of Essential Branch Arteries: An Experimental Model," J Endovasc Surg, 6:171-179 (1999).

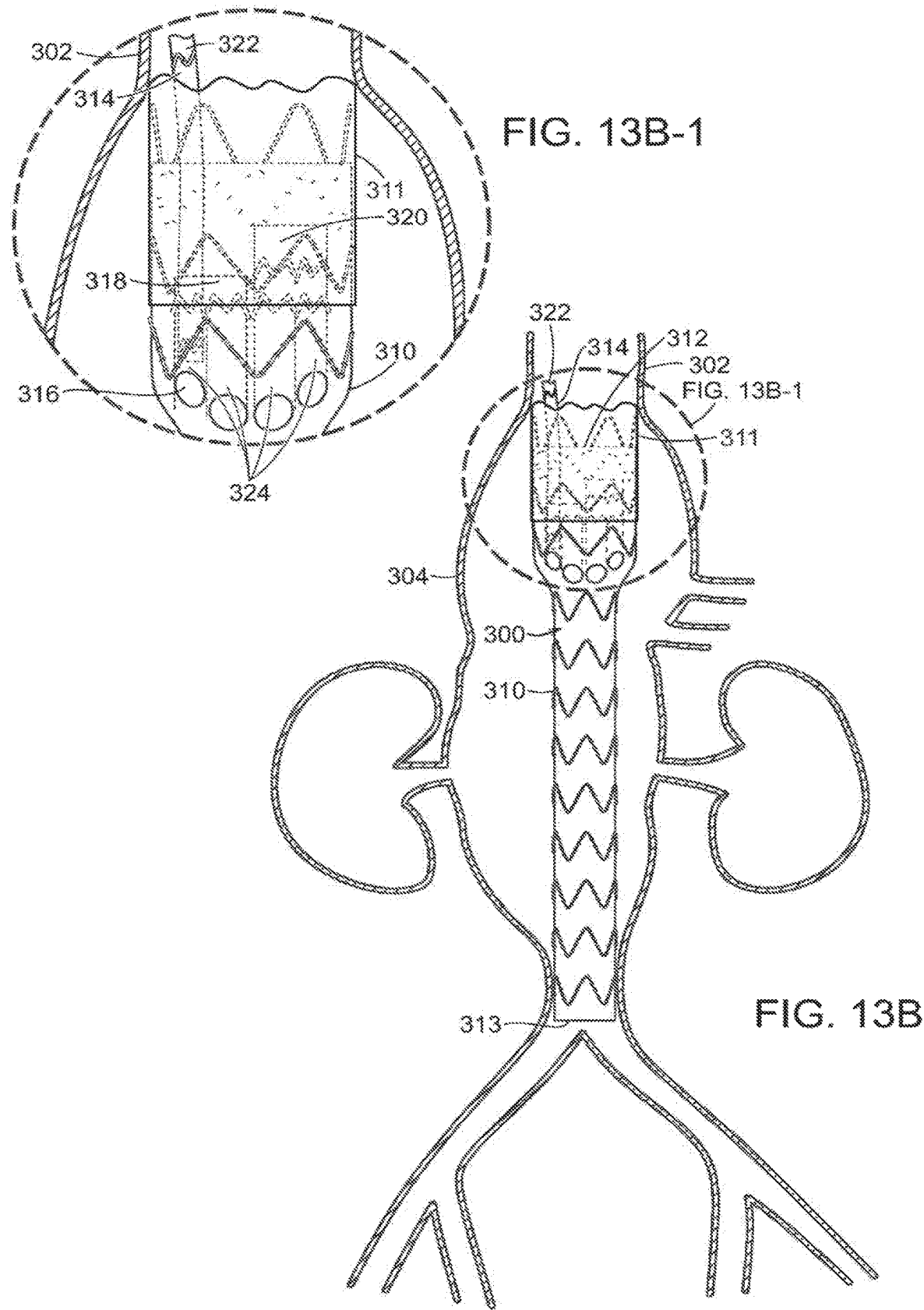

VASCULAR REPAIR DEVICES AND METHODS OF USE

RELATED APPLICATION

This application is a divisional of U.S. application Ser. No. 14/861,479, filed on Sep. 22, 2015, which claims the benefit of U.S. Provisional Application No. 62/054,064, filed on Sep. 23, 2014. The entire teachings of the above applications are incorporated herein by reference.

BACKGROUND OF THE INVENTION

Aortic disease, including aneurysms, penetrating atherosclerotic ulcers and dissections can be life-threatening conditions that occur in different regions of the body. Thoracoabdominal aortic disease generally occurs at the level of the crura of the diaphragm and extends for varying distances proximally, distally or both proximally and distally from the crura. Currently, treatment of thoracoabdominal aortic disease includes, for example, open repair in which the affected portions of the aorta are surgically exposed, or less invasive endovascular repair or hybrid approaches that combine open repair and endovascular treatment. Re-routing of blood vessels that branch from the thoracic and abdominal aorta can be required to main perfusion of and prevent damage to organs in the vicinity of the thoracoabdominal disease. Patients undergoing thoracoabdominal aortic repair are, consequently, at high risk for surgical complications.

Therefore, a need exits for new and improved endovascular repair devices and methods to treat thoracoabdominal aortic disease that improve the efficiency and accuracy of endovascular repair and overcome or minimize the above-referenced problems.

SUMMARY OF THE INVENTION

The present invention relates to vascular repair devices and methods of using the vascular repair devices to treat aortic vascular damage, such as vascular damage associated with thoracoabdominal aortic disease, including aneurysms, penetrating atherosclerotic ulcers and dissection.

In one embodiment, a vascular repair device of the invention includes a main prosthesis having a graft component that includes an external surface and an internal surface, the graft component defining a main lumen, a proximal open end, a distal open end and a first major longitudinal axis extending through the proximal and distal open ends, the main prosthesis also defining at least one fenestration. The vascular repair device includes a first internal prosthesis and a second internal prosthesis within the main lumen. The first internal prosthesis includes a graft component, an external surface and an internal surface, and defines at least in part a first internal lumen, a proximal end located distally to the proximal open end of the main prosthesis, a distal end and a longitudinal axis extending through the first internal lumen, the proximal end and the distal end, and substantially parallel to the first major longitudinal axis. The second internal prosthesis includes a graft component, an external surface and an internal surface, and defines at least in part a second internal lumen, a proximal end located distally to the proximal open end of the main prosthesis, a distal end and a longitudinal axis extending through the second internal lumen, the proximal end and the distal end, and substantially parallel to the first major longitudinal axis. At least two sub-prostheses, each having a graft component define a proximal end, a distal end, at least a portion of a sublumen and a major longitudinal axis extending through the proximal and distal ends and through the sublumen, the graft component of the sub-prostheses each having an external surface and an internal surface, wherein each sublumen extends distally from the distal end of the first internal prosthesis or the second internal prosthesis. The sublumens of each of the sub-prosthesis provide fluid communication between the distal end of at least one of the internal prosthesis and at least one fenestration of the main prosthesis.

In another embodiment, a vascular repair device of the invention includes a main prosthesis having a graft component that includes an external surface and an internal surface, the graft component defining a main lumen, a proximal open end, a distal open end and a first major longitudinal axis extending through the proximal and distal open ends, the main prosthesis also defining at least one fenestration. The vascular prosthesis includes an internal prosthesis within the main lumen that includes a graft component, an external surface and an internal surface, and defines at least in part a first internal lumen, a proximal end located distally to the proximal open end of the main prosthesis, a distal end and a longitudinal axis extending through the first internal lumen, the proximal open end and the distal end, and substantially parallel to the first major longitudinal axis. At least two sub-prostheses, each having a graft component define a proximal end, a distal end, at least a portion of a sublumen and a major longitudinal axis that extends through the proximal and distal ends and through the sublumen, the graft component of the sub-prostheses each having an external surface and an internal surface. Each sub-prosthesis extends distally from the distal end of the internal prosthesis. The sublumens of each of the sub-prosthesis provide fluid communication between the distal end of at least one of the internal prosthesis and the at least one fenestration of the main prosthesis.

In yet another embodiment, a method of the invention for treating aortic vascular damage includes delivering a vascular repair device through a blood vessel to an aneurysm site of a patient and directing at least one additional vascular repair device within a first internal lumen of the vascular repair device. The at least one additional vascular repair device is inserted within at least one of the two sub-prostheses, and a distal end of the at least one additional vascular repair device is inserted into at least one branch vessel of the blood vessel, to thereby treat aortic vascular damage at the aneurysm site of the patient.

The vascular repair device and method of the invention for treating aortic vascular damage have many advantages. For example, the vascular repair devices and methods of the invention to treat aortic disease, such as aortic aneurysms at, near or around the thoracoabdominal aorta, provides the surgeon with a graduated margin of error during in situ assembly of modular vascular repair devices by stepped cannulation while directing components of vascular repair devices into place, in and around the site of the aneurysm. Thus, the aortic graft assembly, delivery systems, and methods of the invention can be used to treat various aortic pathologies, including aortic aneurysms, penetrating atherosclerotic ulcers and dissections of, and proximate to, for instance, the celiac, superior mesenteric and renal arteries while significantly reducing the likelihood of complications and death.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 13A, 13B-1, 13B, 13B-2 and 13C show placement of an embodiment of a vascular repair device of the invention into the aorta in an embodiment of a method of the invention.

DETAILED DESCRIPTION OF THE INVENTION

Figure 1:
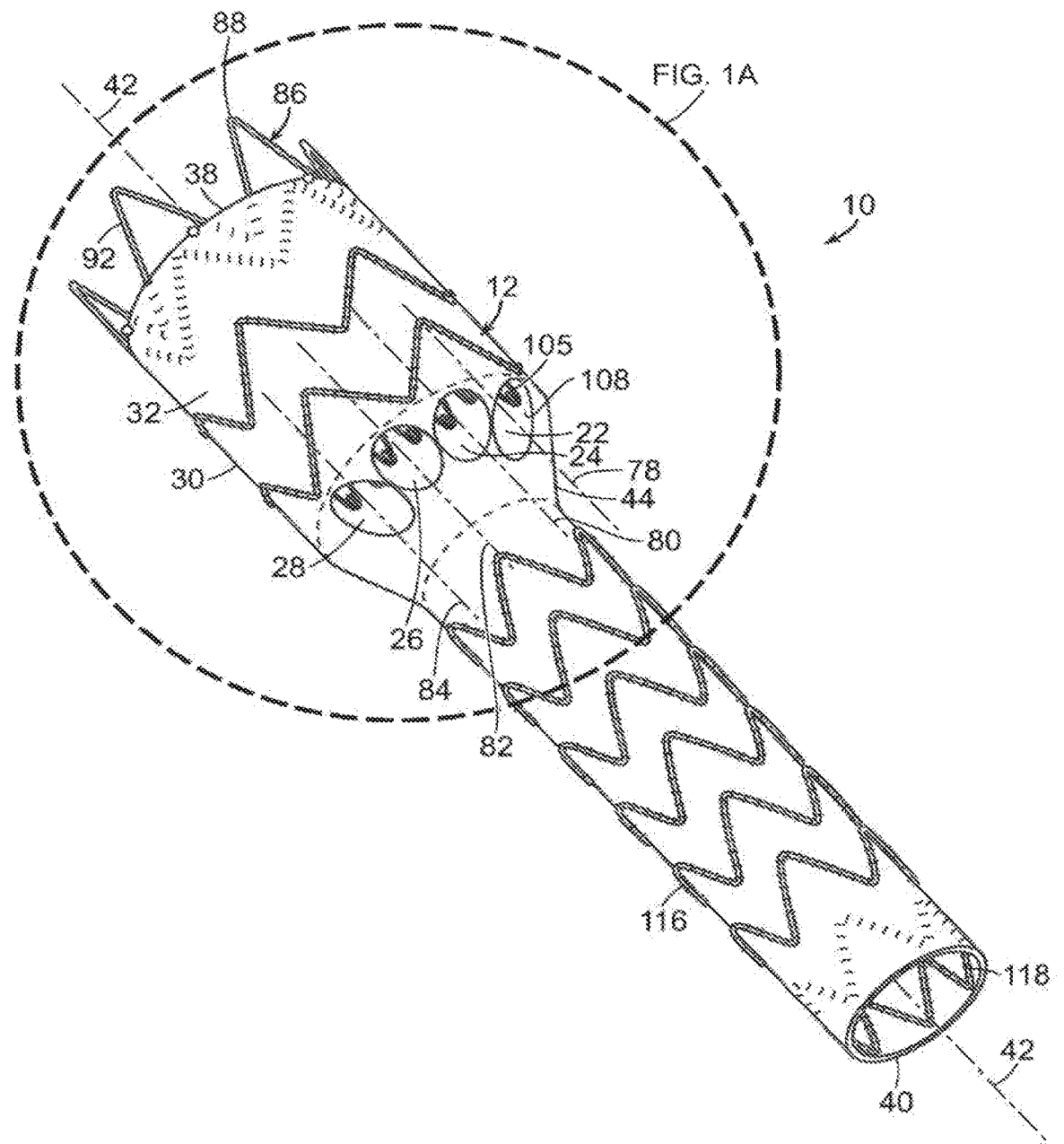
FIG. 1 is a perspective view of one embodiment of a vascular repair device of the invention.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

When reference is made herein to a prosthesis to be delivered, or implanted in a patient, such as vascular repair device, the word "proximal" means that portion of the prosthesis or component of the prosthesis that is towards the heart of the patient and "distal" means that portion of the prosthesis or component of the prosthesis that is away from the heart of the patient.

When, however, reference is made to a delivery system or a component of a delivery system employed to deliver, or implant a vascular repair device, such as a nose cone or handle of a delivery device, the word, "proximal," as employed herein, means closer to the clinician using delivery system. Likewise, "distal" means, when reference is made to a delivery system or a component of a delivery system, such as a nose cone or handle of a delivery device, means further away from the clinician using the delivery system.

For clarity, the word "proximate" means close to as opposed to the meanings ascribed to "proximal" or "distal" as described above with respect to either the vascular repair device or delivery system.

Vascular repair devices of the invention can be implanted, for example, by transfemoral access. Additional vascular repair devices that are directed into the vascular repair devices of the invention can be implanted, for example, by supraaortic vessel access (e.g., through the brachial artery), or by transfemoral or transapical access, or by access from some other branches of major blood vessels, including peripheral blood vessels.

The invention is generally directed to vascular repair devices and methods for treating aortic vascular damage. In one embodiment of a vascular repair device of the invention, represented in FIGS. 1, 1A and 2, vascular repair device 10 includes main prosthesis 12, first internal prosthesis 14, corresponding sub-prostheses 18,19, second internal prosthesis 16 and corresponding sub-prostheses 20, 21. Main prosthesis 12 also defines at least one fenestration, such as fenestrations 22,24,26 and 28. First internal prosthesis 14, second internal prosthesis 16 and respective sub-prostheses 18,19,20 and 21 are affixed to main prosthesis 12 by a suitable method, such as, for example, by use of sutures (not shown).

Main prosthesis 12 includes graft component 30 that includes external surface 32 and internal surface 34. Graft component 30 of main prosthesis 12 defines main lumen 36, proximal open end 38, distal open end 40 and first major longitudinal axis 42 extending through the proximal open end 38 and distal open end 40. Examples of suitable diameters of the main prosthesis are diameters in a range of between about 20 mm and about 50 mm. Examples of suitable lengths of the main prosthesis are lengths in a range of between about 40 mm and about 200 mm.

Distal open end 40 of main prosthesis 12 has a cross-sectional area that is smaller than that of proximal open end 38 of main prosthesis 12. In a typical embodiment, the cross-sectional area of distal open end 40 of main prosthesis 12 is in a range of between about 12 mm and about 36 mm.

Graft component 30 of main prosthesis 12 includes midsection 44 that narrows in a distal direction along main lumen 36. The portion of main prosthesis 12 that extends in a proximal direction along main lumen 36 from midsection 44 can be a length in a range of about 30 mm to about 120 mm. The portion of the main prosthesis 12 that extends in a distal direction along main lumen 36 from midsection 44 can be a length in a range of about 10 mm to about 80 mm.

Figure 1A:
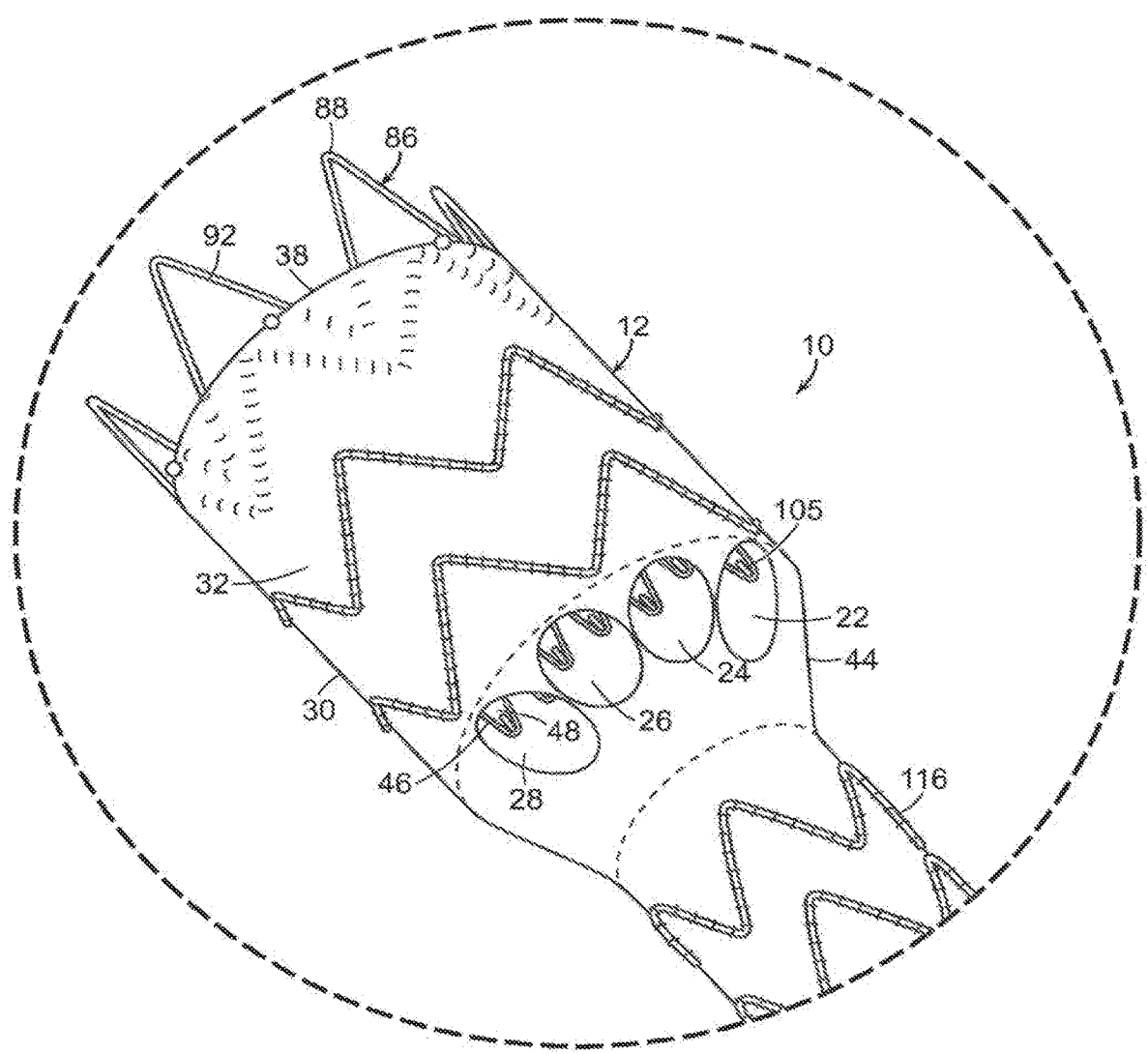
FIG. 1A is a detail of the embodiment of a vascular repair device of the invention taken from FIG. 1.

At least one stent 46 at distal end of graft component of at least one sub-prostheses is internal to sub-prosthesis and includes at least one active fixation component, such as barb 48, as can be seen in FIGS. 1 and 1A.

Figure 2:
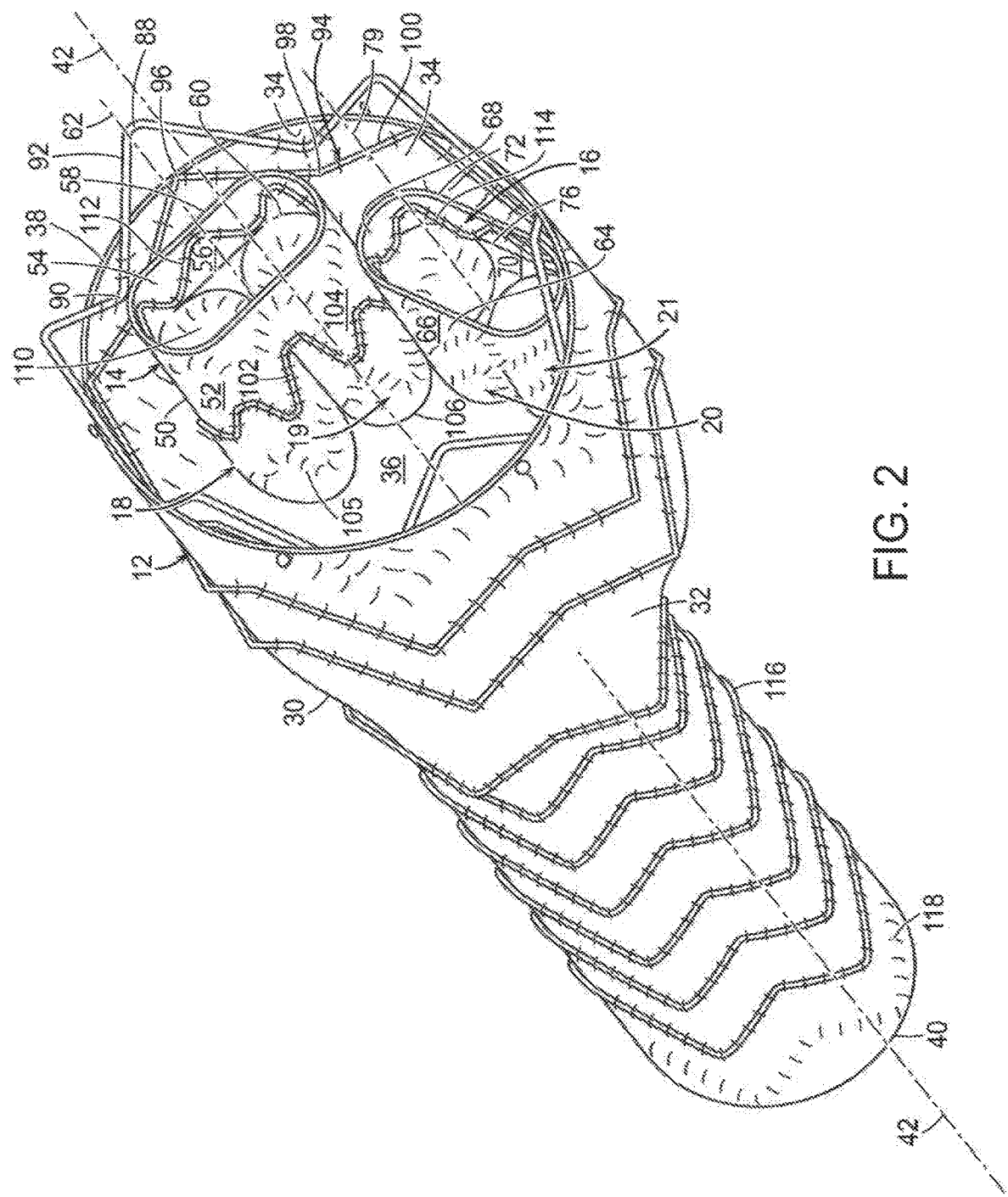
FIG. 2 is another perspective view, into a proximal open end, of the embodiment of the vascular repair device of the invention of FIG. 1.

As can be seen in FIG. 2, first internal prosthesis 14 is within main lumen 36 of main prosthesis 12. First internal prosthesis 14 includes graft component 50, external surface 52 and internal surface 54, defining at least in part first internal lumen 56 and proximal end 58. Proximal end 58 is located distally to proximal open end 38 of main prosthesis 12. First internal prosthesis 14 also includes distal end 60 and defines longitudinal axis 62 extending through first internal lumen 56, proximal end 58 and distal end 60 of first internal prosthesis 14, and is substantially parallel to first major longitudinal axis 42 of main prosthesis.

Second internal prosthesis 16 is within main lumen 36 of main prosthesis 12. Second internal prosthesis 16 includes graft component 64, external surface 66 and internal surface 68, and defines at least in part second internal lumen 70. Proximal end 72 of second internal prosthesis 16 is located distally to proximal end 38 of main prosthesis 12. Longitudinal axis 79 of second internal prosthesis 16 extends through second internal lumen 70, proximal end 72 and distal end 76, and is substantially parallel to first major longitudinal axis 42 of main prosthesis 12.

Proximal end 72 of second internal prosthesis 16 is distal to proximal end 58 of first internal prosthesis 14. However, the position of proximal end 58 of first internal prosthesis 14 and proximal end 72 of second internal prosthesis 16 can vary relative to each other. For example, alternatively, proximal end 72 of second internal prosthesis 16 can be proximal, distal or at substantially equal distance from proximal open end 38 of graft component 30 of main prosthesis 12 as proximal end 58 of first internal prosthesis 14. Examples of suitable ranges of lengths of first internal prosthesis 14 and second internal prosthesis 16 are between about 10 mm and about 30 mm.

At least one fenestration is at midsection 44 of main prosthesis 12, such as two, three or four fenestrations. Midsection 44 defines four independent fenestrations 22,24, 26 and 28. Sub-prostheses 18,19 of first internal prosthesis 14 extend from distal end 60 of first internal prosthesis 14 to first fenestration 22 and second fenestration 24, respectively at midsection 44 of main prosthesis 12, and sub-prostheses 20,21 extend from second internal prosthesis 16 to third fenestration 26 and fourth fenestration 28 at midsection 44 of main prosthesis 12. Sub-prostheses 18,19,20 and 21 define, respectively, major longitudinal axes 78,80,82 and 84, all of which are substantially parallel to major longitudinal axis 42.

Vascular repair device 10 includes stent 86 having proximal apices 88 and distal apices 90 connected by struts 92 at proximal open end 38 of main prosthesis 12. Stent 86 is affixed to internal surface 34 but, alternatively, can be affixed to external surface 32 (not shown).

Additional stent 94 has proximal 96 and distal 98 apices connected by struts 100 and is distal to stent 86 at proximal open end 38 of main prosthesis 12. In a preferred embodiment, distal apices 90 of stent 86 are nested between proximal apices 96 of additional stent 94 at proximal open end 38 of graft component 30 of main prosthesis 12. "Nesting," as that term is employed herein, means that proximal apices 96 of additional stent 94, for example, are proximal to distal apices 90 of proximal stent 86. Stents 112,114 are located within first internal prostheses 14,16, respectively. Additional stents 116 are located along main prosthesis 12. Distal stent 118 is located within main graft component 30 at distal end 40.

Sub-prostheses 18,19 also can include stents having distal and proximal apices linked by struts. Further, each of internal prostheses and sub-prostheses can include, independently, one or more stents, located internally or externally of the respective graft component to which each is attached. For example, vascular repair device 10 can include at least one stent 102 at each of proximal end 104 and stent 105 at distal end 106 of sub-prostheses 18. Stent 105 at distal end 106 of sub-prostheses 19 is at respective fenestration 22 with which graft component 108, defining sublumen 110, is in fluid communication.

Radiopaque markers 119 extend about proximal open end 38.

Suitable materials of graft components of vascular repair device 10 of the invention can include, for example, polyester and polytetrafluoroethylene. Stents employed in the invention are of a suitable material. In one embodiment, the stents employed by the invention are composed of a suitable shape memory alloy, such as nitinol. Stents employed in the intervention can be affixed to the graft component, such as by sewing. Further description of suitable materials for construction of stents for use in the vascular repair devices of the invention and methods of making stents can be found in U.S. Pat. Nos. 7,763,063; 8,007,605 and 8,062,345, the teachings of which are incorporated herein by reference in their entirety.

Figure 3:
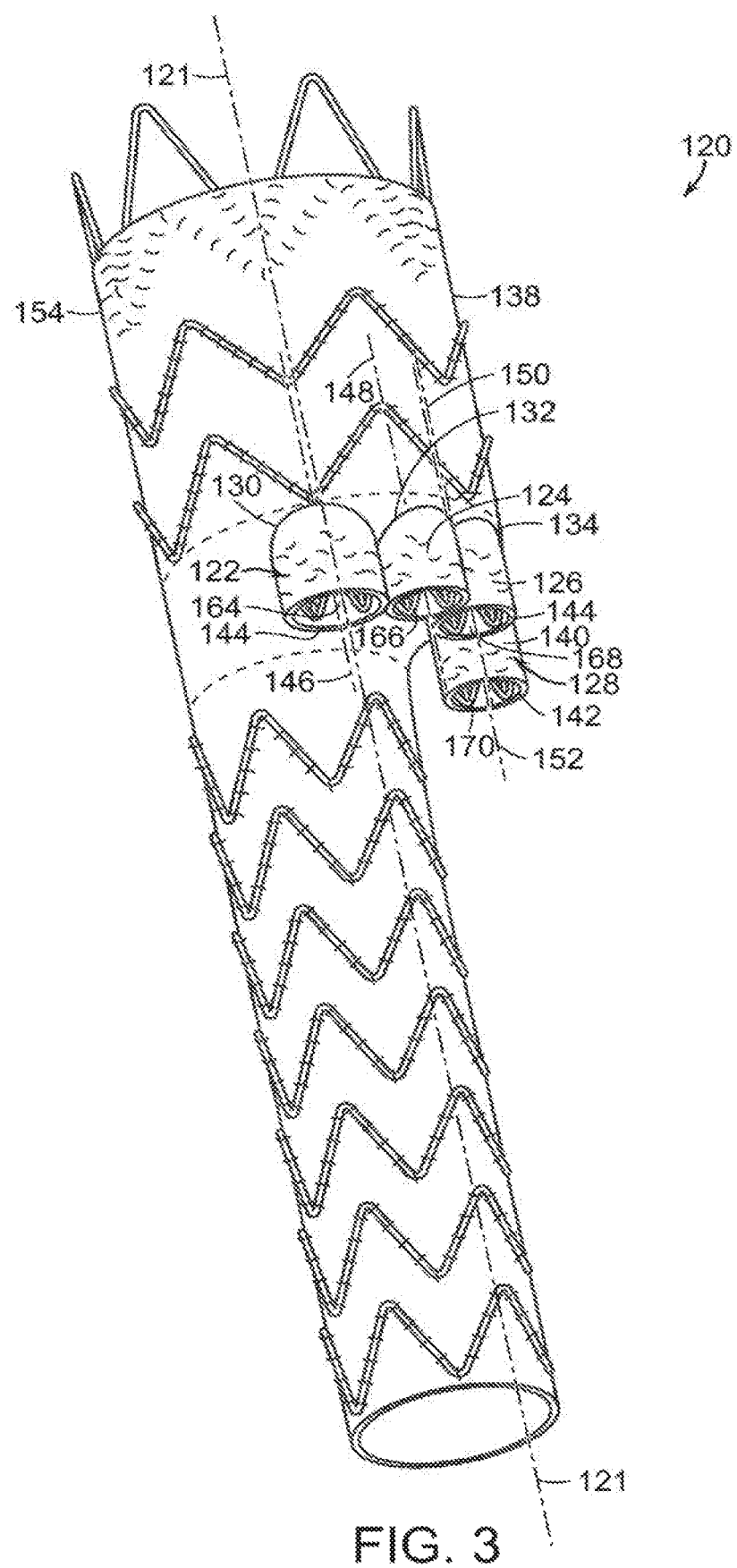
FIG. 3 is a perspective view of another embodiment of a vascular repair device of the invention.

In another embodiment, shown in FIG. 3, vascular repair device 120 includes main prosthesis 154 that defines major longitudinal axis 121. Vascular repair device 120 includes sub-prostheses 122,124,126 and 128 that extend through respective fenestrations 130,132,134 and 136 of main graft component 138 can vary in length, relative to each other. Also, examples of suitable ranges of diameters of the sub-prostheses are between about 6 mm and about 10 mm. Examples of suitable ranges of lengths of the sub-prostheses are between about 5 mm and about 30 mm. Sub-prosthesis 128, for example, includes graft component 140 and distal end 142. Distal end 142 of graft component 140 of sub-prosthesis 128 extends distally beyond distal end 144 of at least one of another of sub-prostheses, such as sub-prosthesis 122. Also shown in FIG. 3, as another example, distal end 144 of sub-prostheses 122 can have a different diameter than distal end of another of at least one of the sub-prostheses, such as distal end 142 of sub-prosthesis 128. For example, the distal end of one sub-prosthesis can have a diameter than differs from the distal end of at least one other sub-prosthesis in a range of about 6 mm to about 10 mm.

Figure 4:
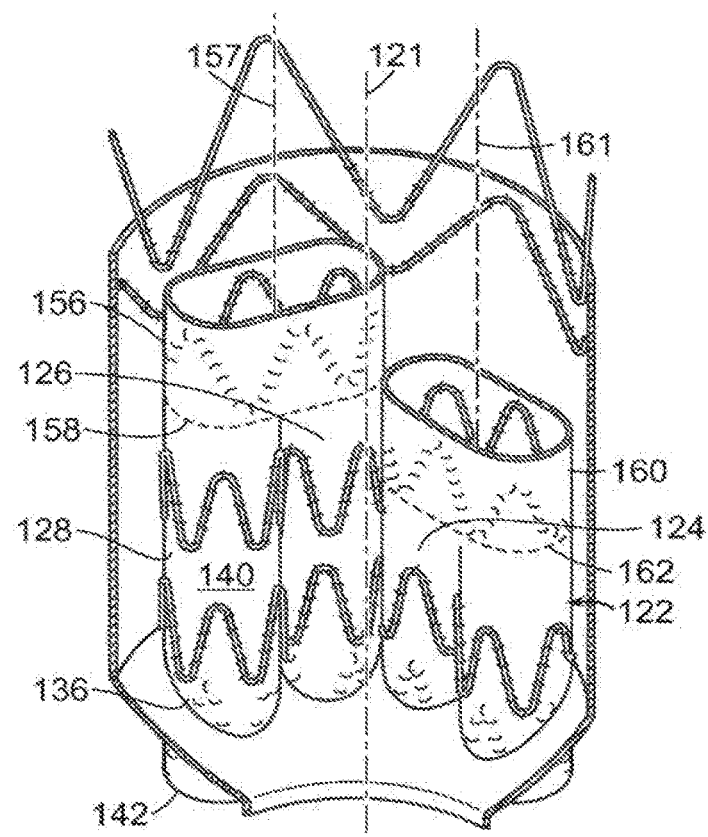
FIG. 4 is a cut-away view, in perspective, of a proximal open end of the embodiment of the vascular repair device of the invention of FIG. 3.

As can be seen in FIGS. 3 and 4, each graft component of each sub-prosthesis defines a proximal end, a distal end and at least a portion of a sublumen. Major longitudinal axes 146, 148,150 and 152 of sub-prostheses 122,124,126 and 128, respectively, extend through the respective proximal end, distal end and sublumen of each sub-prosthesis and are substantially parallel to major longitudinal axis 121. The graft component of each sub-prosthesis also has an external surface and internal surface. The distal ends of sub-prostheses 122,124,126 and 128 extend through fenestrations 130, 132,134 and 136, respectively, that are defined by main prosthesis 154 of vascular repair device 120. First internal prosthesis 156 defines major longitudinal axis 157 and second internal prosthesis 160 defines major longitudinal axis 161. Major longitudinal axes 157,161 and substantially parallel to major longitudinal axis 121. Each sub-prosthesis 122,124,126 and 128 extends distally from first internal prosthesis 156 at distal end 158 or from second internal prosthesis 160 at distal end 162. In both embodiments, sublumens 164,166,168 and 170 of sub-prostheses 122,124, 126 and 128, respectively, provide fluid communication between first internal prosthesis 156 and second internal prosthesis 160 and fenestrations 130,132,134 and 136 of main prosthesis 154.

Figure 5:
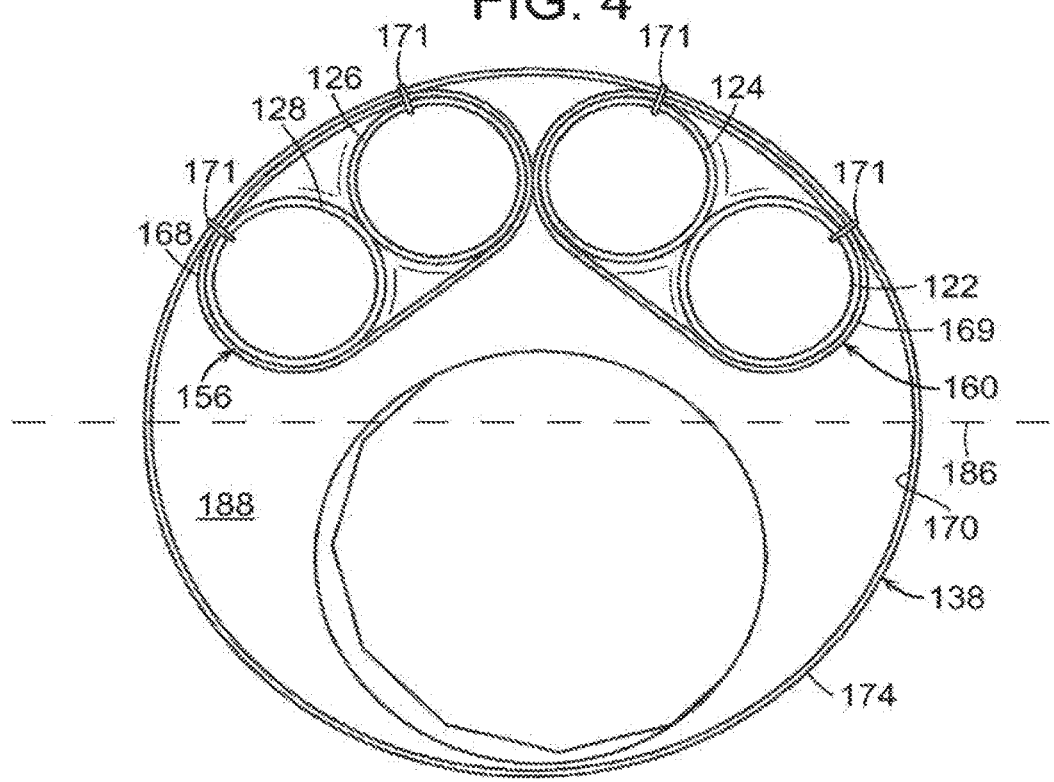
FIG. 5 is an end view of one embodiment of a vascular repair device of the invention.

As can be seen in FIG. 5, at least a portion of external surface 168,169 of the graft component of at least one of first internal prosthesis 156 and second internal prosthesis 160 is affixed by a suitable method to a portion of internal surface 170 of main graft component 138. Examples of suitable methods for affixing internal prostheses 156,160 to internal surface 170 of main graft component 138 include, sutures 171, and glue.

Figure 6:
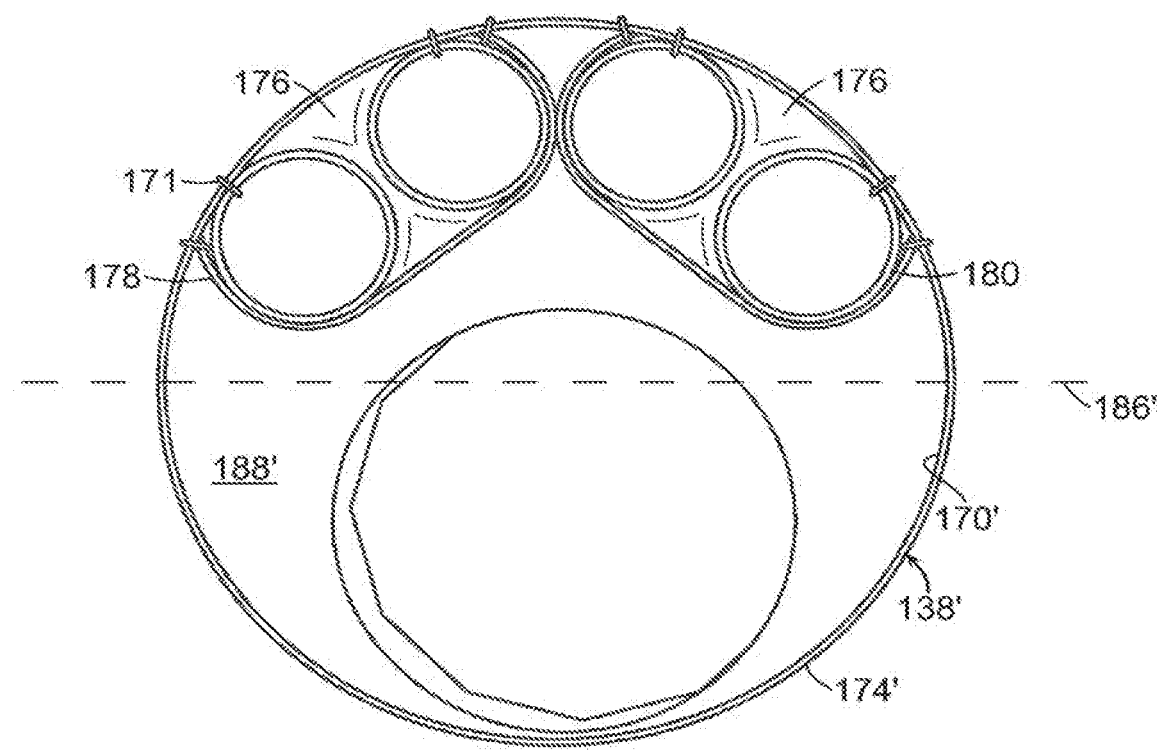
FIG. 6 is an end view of another embodiment of a vascular repair device of the invention.

As can be seen in FIG. 6, in another embodiment of the invention, a portion of internal surface 170' of main graft component 138' of main prosthesis 174' defines a portion of internal lumen 176 of at least one of first internal prosthesis 178 and second internal prosthesis 180, thereby reducing the profile and increasing the flexibility of the vascular repair device for implantation in a patient.

Figure 7:
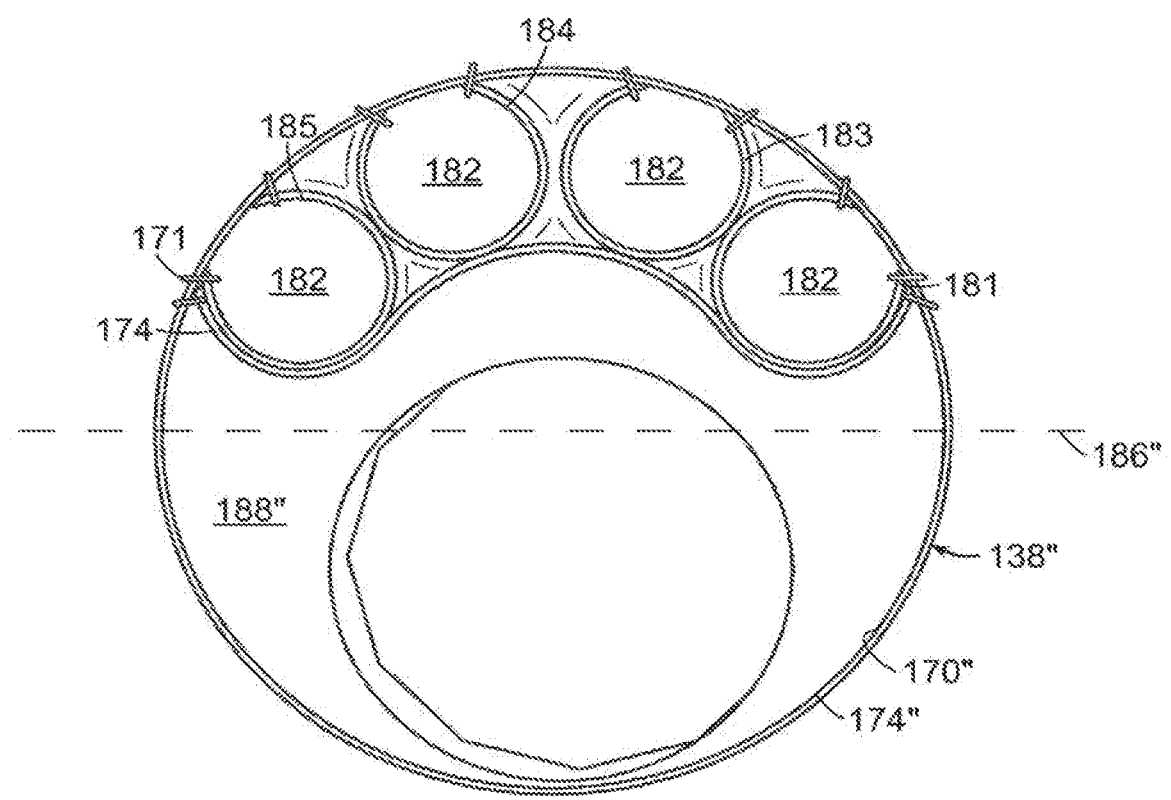
FIG. 7 is an end view of yet another embodiment of a vascular repair device of the invention.

Similarly, a portion of the internal surface 170" of main graft component 138" defines at least a portion of sublumen 182 of respective sub-prostheses 181,183,184 and 185 within internal prosthesis 174" as shown in FIG. 7.

As shown in FIGS. 5-7, proximal ends of first and second internal prostheses are on a side of plane 186 longitudinally bisecting main lumen 188,188',188" defined by main graft component 138,138',138", respectively. In certain embodiments of the invention, at least one of the first internal lumen and the second internal lumen has a cross-section that is non-circular, such as an oval-shape. In another embodiment, proximal ends of first and second internal prostheses have a non-circular shape resembling a race-track, where the minor axis has a width of between about 6 mm and 10 mm and the major axis has a length that is approximately double the width of the minor axis with a range of between about 12 mm and about 20 mm (not shown). In the embodiments shown in FIGS. 5-7, all of the openings of the sub-prostheses each have a cross section that is approximately circular. In an alternative embodiment, a cross-section of a combination of two sublumens of the at least two sub-prostheses approximates an oval shape. In still another embodiment, the graft component of the sub-prostheses defines an opening at its proximal end that is at least approximately circular (not shown).

Figure 8:
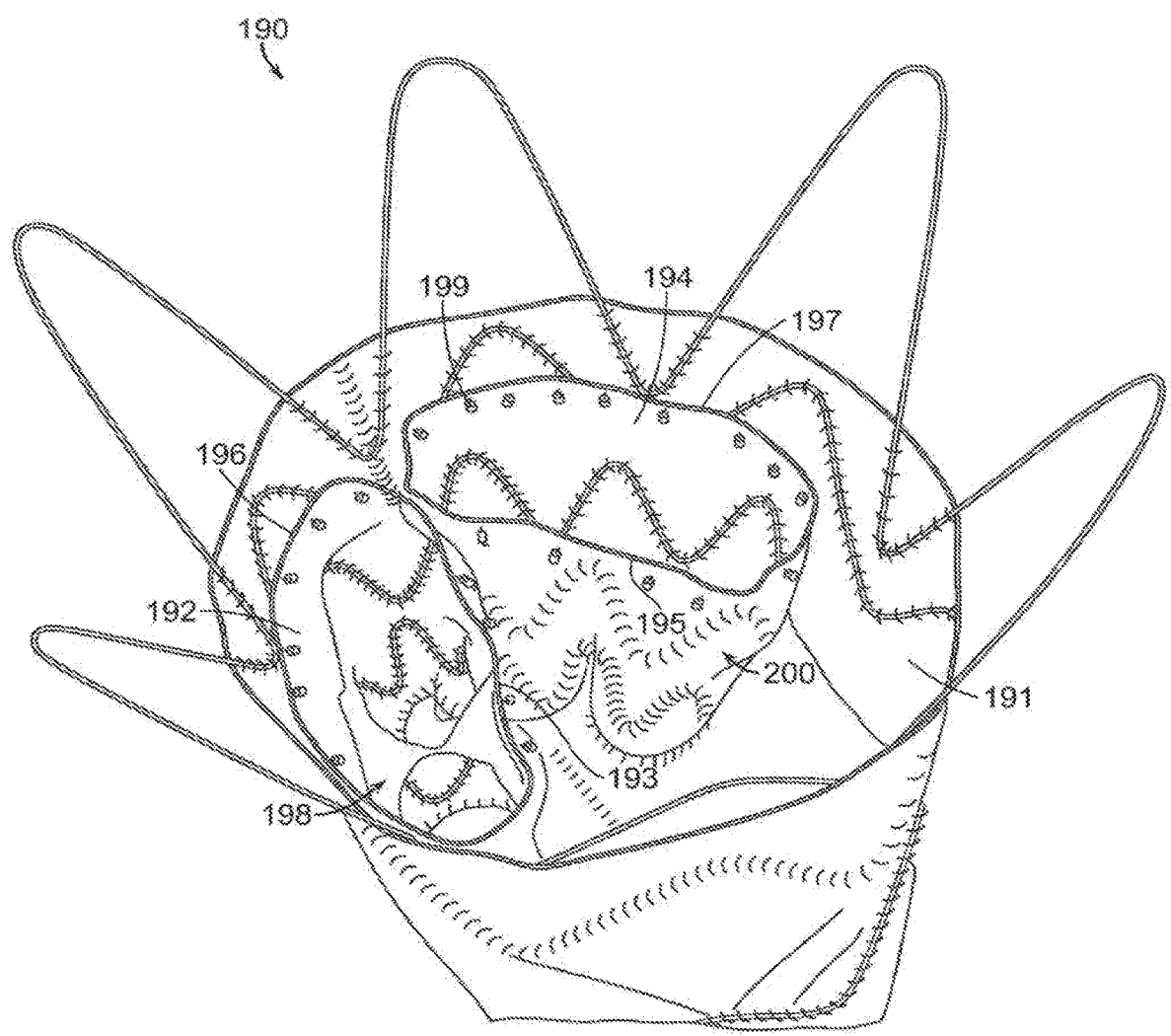
FIG. 8 is a perspective view into a proximal open end of still another embodiment of a vascular repair device of the invention.

In one embodiment, shown in FIG. 8, vascular repair device 190 includes portions 192,194 of respective proximal ends 196,197 of first internal prosthesis 198 and second internal prosthesis 200, respectively, contact main graft component 191 and are proximal to the remainder 193,195 of proximal ends 196,197 of respective first internal prosthesis 198 and second internal prosthesis 200. Radiopaque markers 199 extend about proximal open end 196,197 of first internal prosthesis 198 and second internal prosthesis 200.

Figure 9:
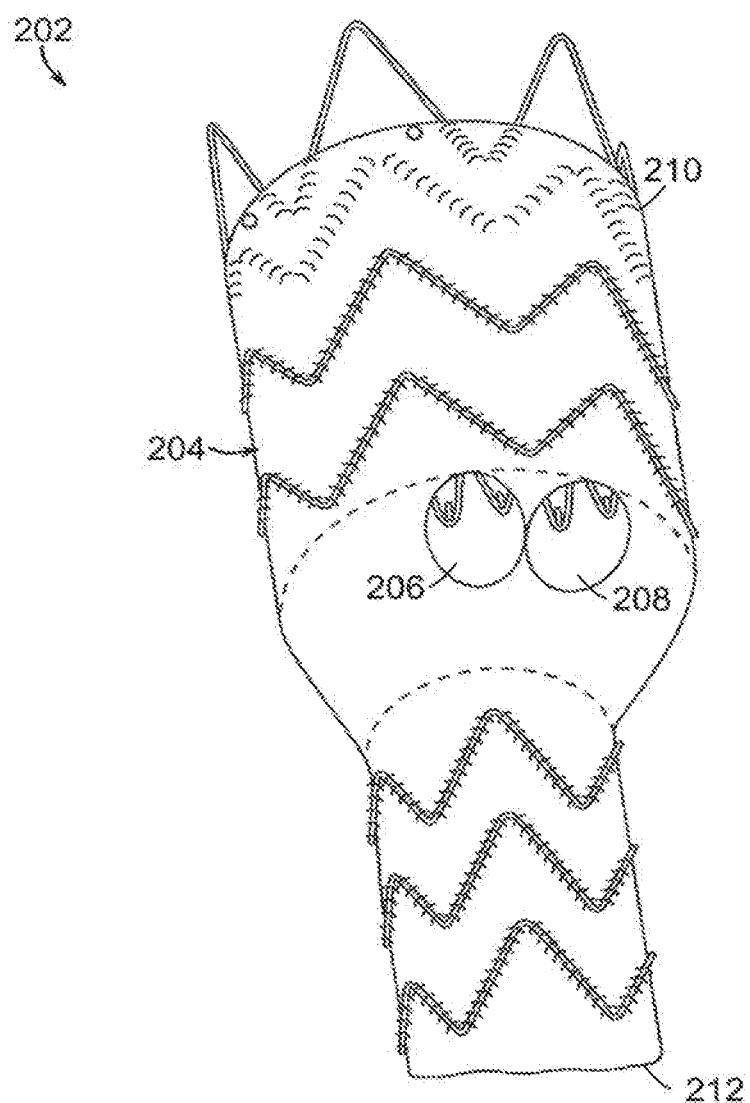
FIG. 9 is a perspective view of a portion of an embodiment of a vascular repair device of the invention having two fenestrations at a midsection of the device.
Figure 10A:
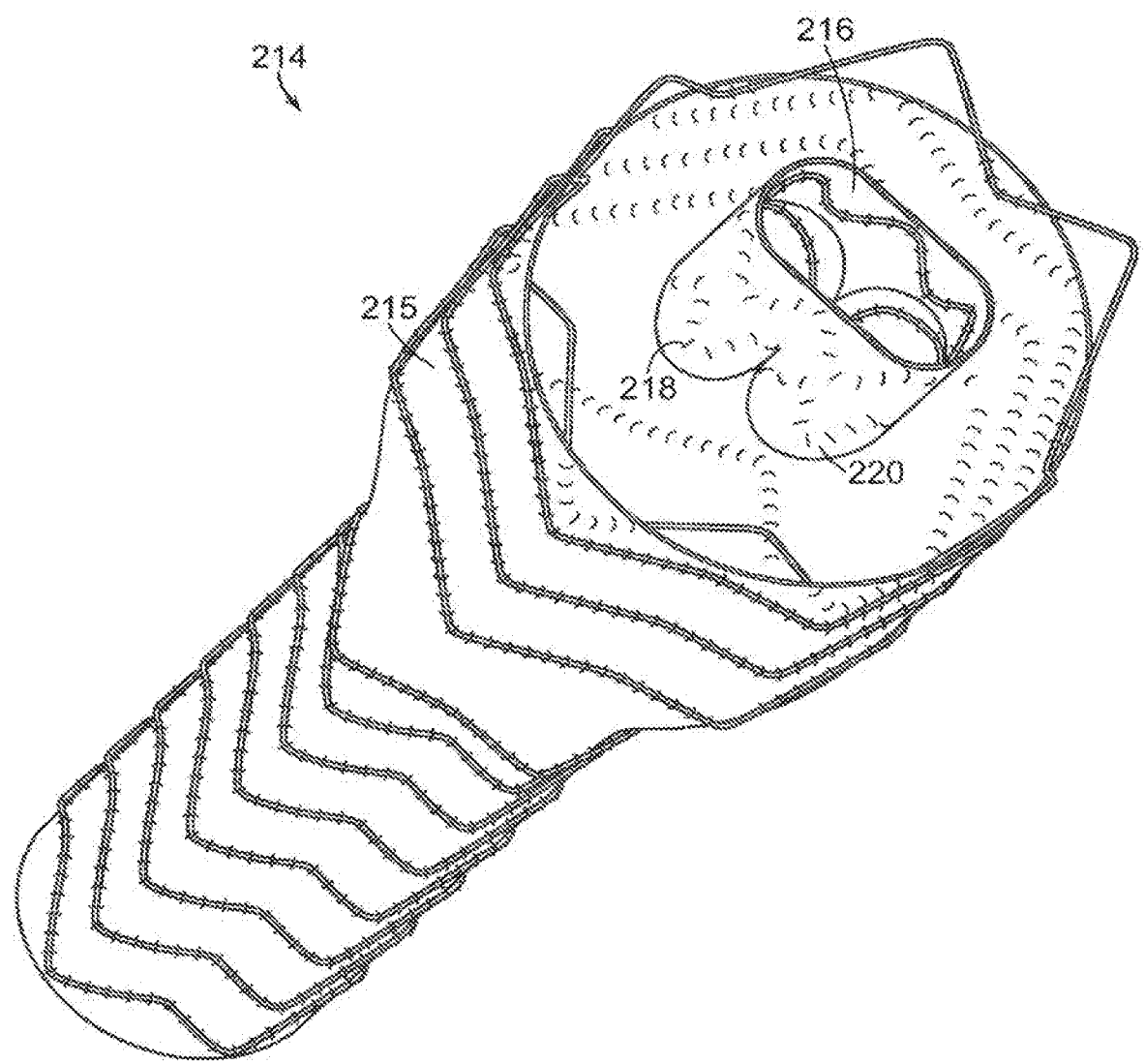
FIG. 10A is a perspective view into a proximal open end of one embodiment of a vascular repair device of the invention.
Figure 10B:
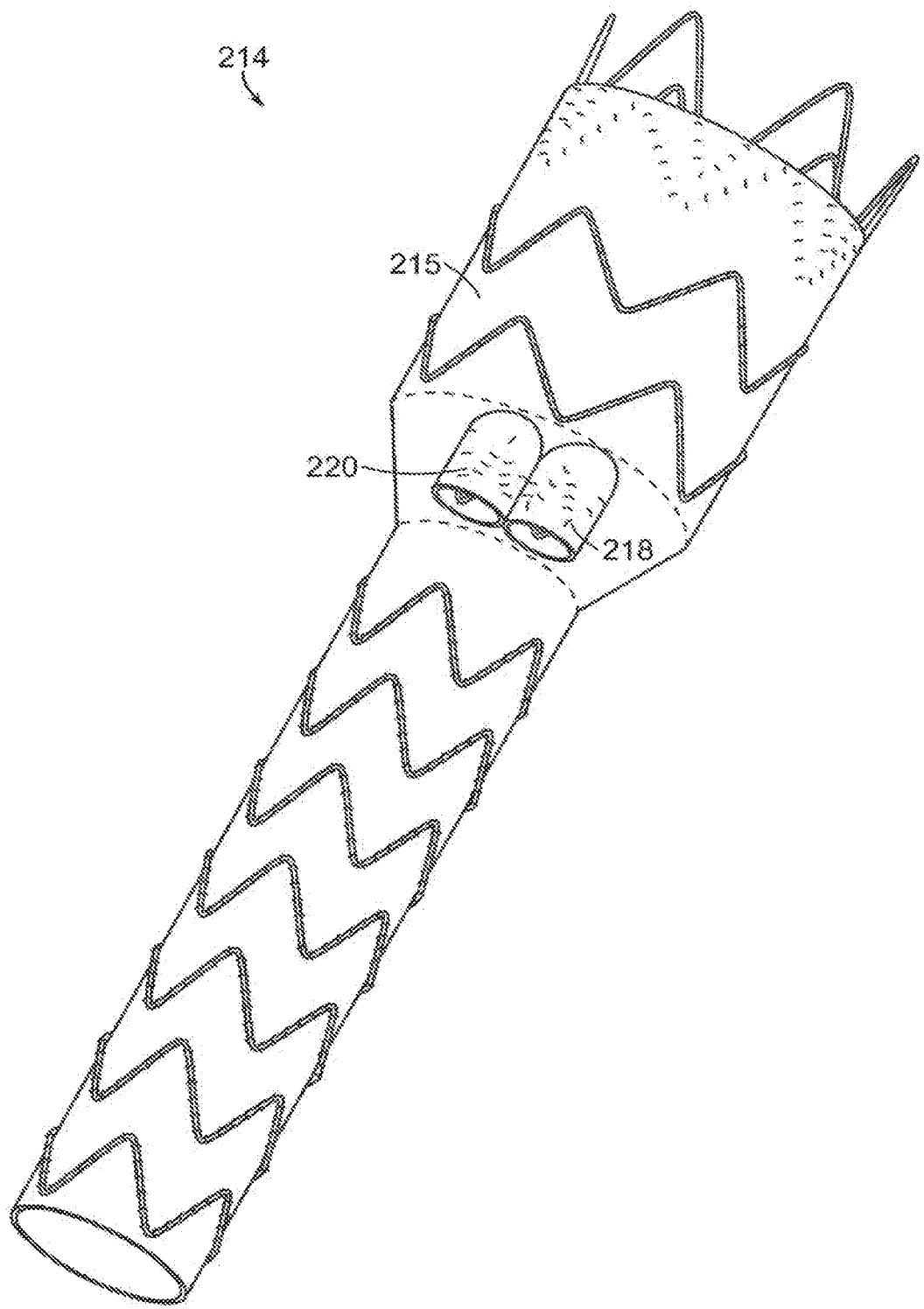
FIG. 10B is another perspective view of an embodiment of the vascular repair device of the invention of FIG. 10A.

As shown in FIG. 9, vascular repair device 202 includes main prosthesis 204 that defines two fenestrations 206,208 between proximal open end 210 and distal open end 212. In another embodiment, the main prosthesis of the vascular repair device defines three fenestrations between the proximal open and distal open end (not shown). Vascular repair device 214 of FIGS. 10A and 10B includes main prosthesis 215, internal prosthesis 216 and at least two sub-prostheses 218,220.

Figure 11A:
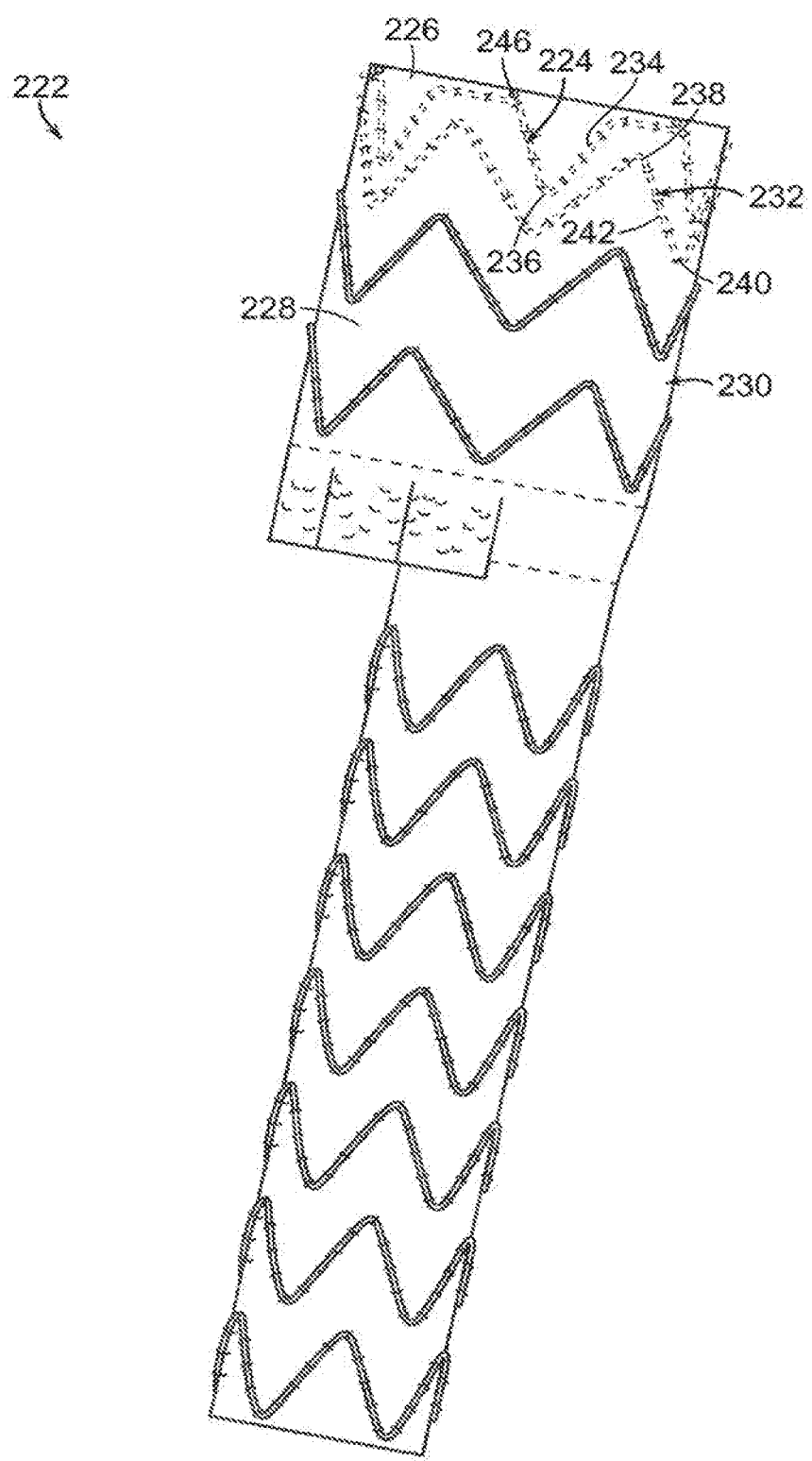
FIG. 11A is a side view of another embodiment of a vascular repair device of the invention.
Figure 11B:
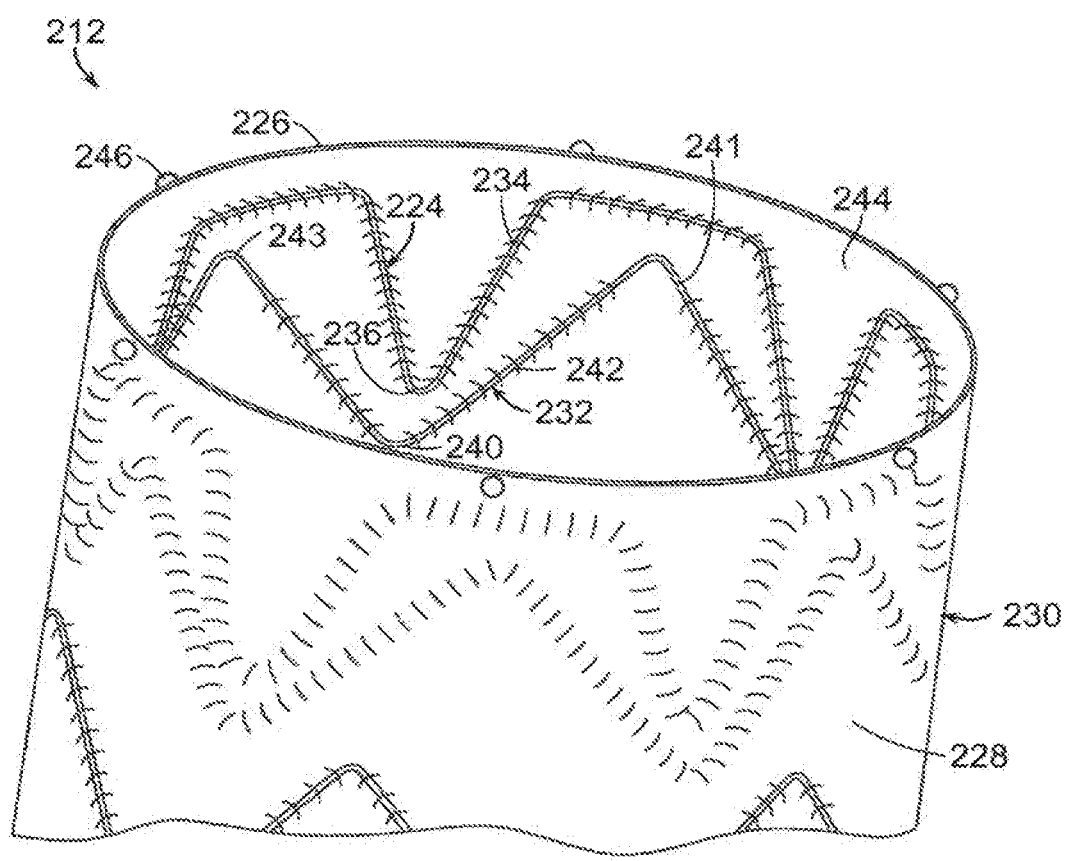
FIG. 11B is a perspective view into a proximal open end of the embodiment of the vascular repair device of the invention of FIG. 11A.

In another embodiment, shown in FIGS. 11A and 11B, vascular repair device 222 includes crown stent 224 at proximal open end 226 of graft component 228 of main prosthesis 230, and clasping stent 232 distal to crown stent 224. Crown stent 224 includes struts 234 and distal apices 236 joining the struts 234, and clasping stent 232 includes proximal apices 238, distal apices 240 and struts 242 connecting proximal apices 238 and distal apices 240. In one embodiment, crown stent 224 is attached in its entirety to internal surface 244 of proximal open end 226 of main prosthesis 230. Clasping stent 232 is attached to internal surface 244 of main prostheses 230. In a preferred embodiment, crown stent 224 is affixed to internal surface 244 at proximal open end 226 and clasping stent 232 is affixed at least in part to internal surface 244 distal to crown stent 224. Distal apices 236 of crown stent 224 are nested between proximal apices 238 of clasping stent 232 and at least one proximal apex 238 of clasping stent 232 is unattached from internal surface 244 of proximal open end 226 of main prosthesis 230. At least two of the proximal apices of clasping stent 232 are unattached portions 241, 243. Radiopaque markers 246 extend about proximal open end 226.

Figure 12:
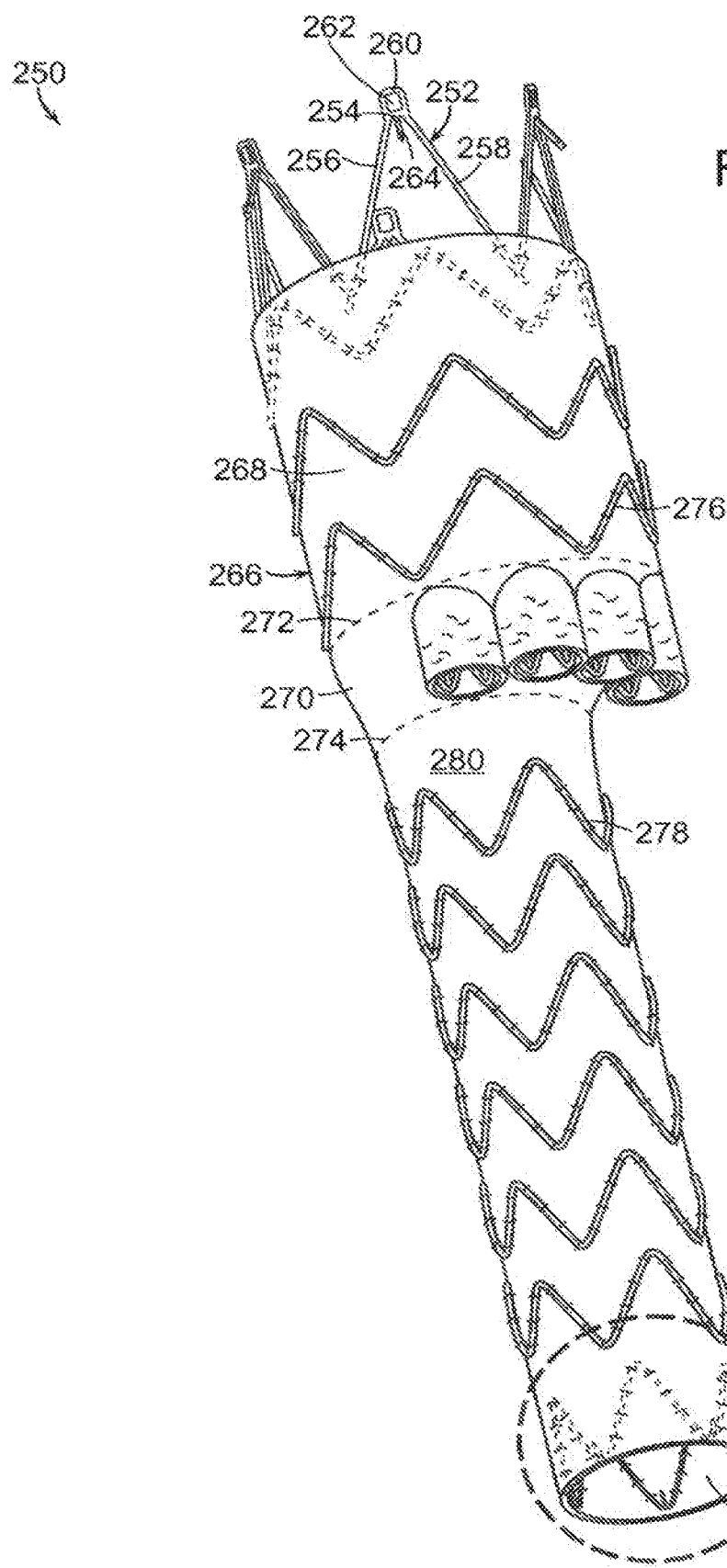
FIG. 12 is a perspective view of still another embodiment of an embodiment of a vascular repair device of the invention.
Figure 12A:
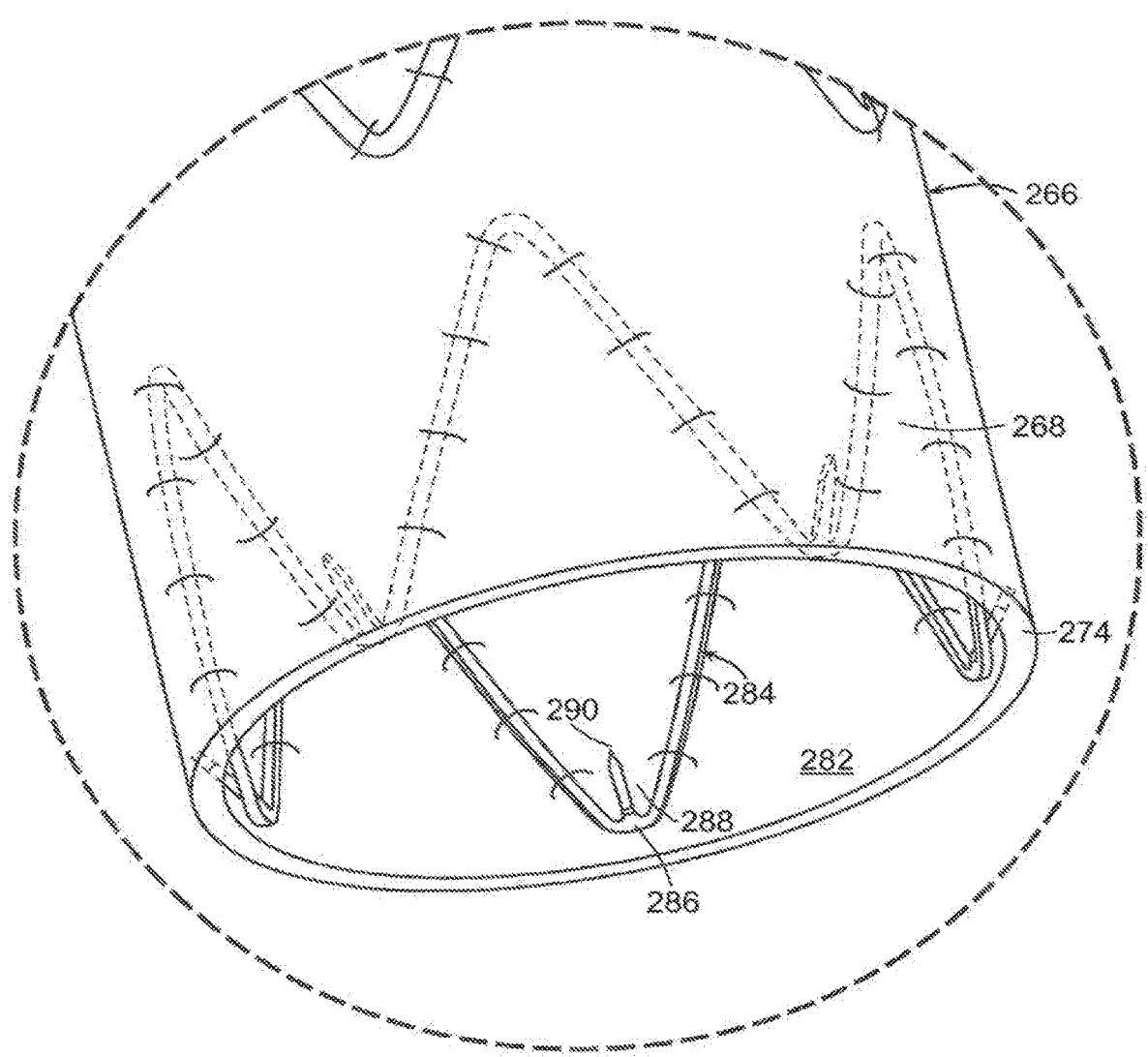
FIG. 12A is a detail of the perspective view, into a distal open end, of the embodiment of the vascular repair device of the invention shown in FIG. 12.

In another embodiment, shown in FIGS. 12 and 12A, vascular repair device 250 includes at least one stent of main prosthesis having active fixation components. Active fixation components of vascular repair device 250 include, for example, at least one barb, as shown in FIG. 12. In one embodiment, proximal stent 252 of vascular repair device 250 includes bridge 254 that spans adjacent struts 256,258 extending from respective proximal apex 260, thereby defining eyelet 262. Barb 264 extends from bridge 254.

Main prosthesis 266 of vascular repair device 250 includes graft component 268 and midsection 270 having proximal end 272 and distal end 274. Stents 276,278 are at each of proximal end 272 and distal end 274 of midsection 270 of graft component 268 of main prosthesis 266. Stents distal 278 and proximal 276 to midsection 270 can be secured to external surface 280 or internal surface 282 of main prosthesis 266.

As shown in FIG. 12A, stent 284 at distal end 274 of main prosthesis 266 is attached to internal surface 282 of graft component 268 of main prosthesis 266. An active fixation component, such as barb 290, extends proximally from distal apex 286.

Figure 13A:
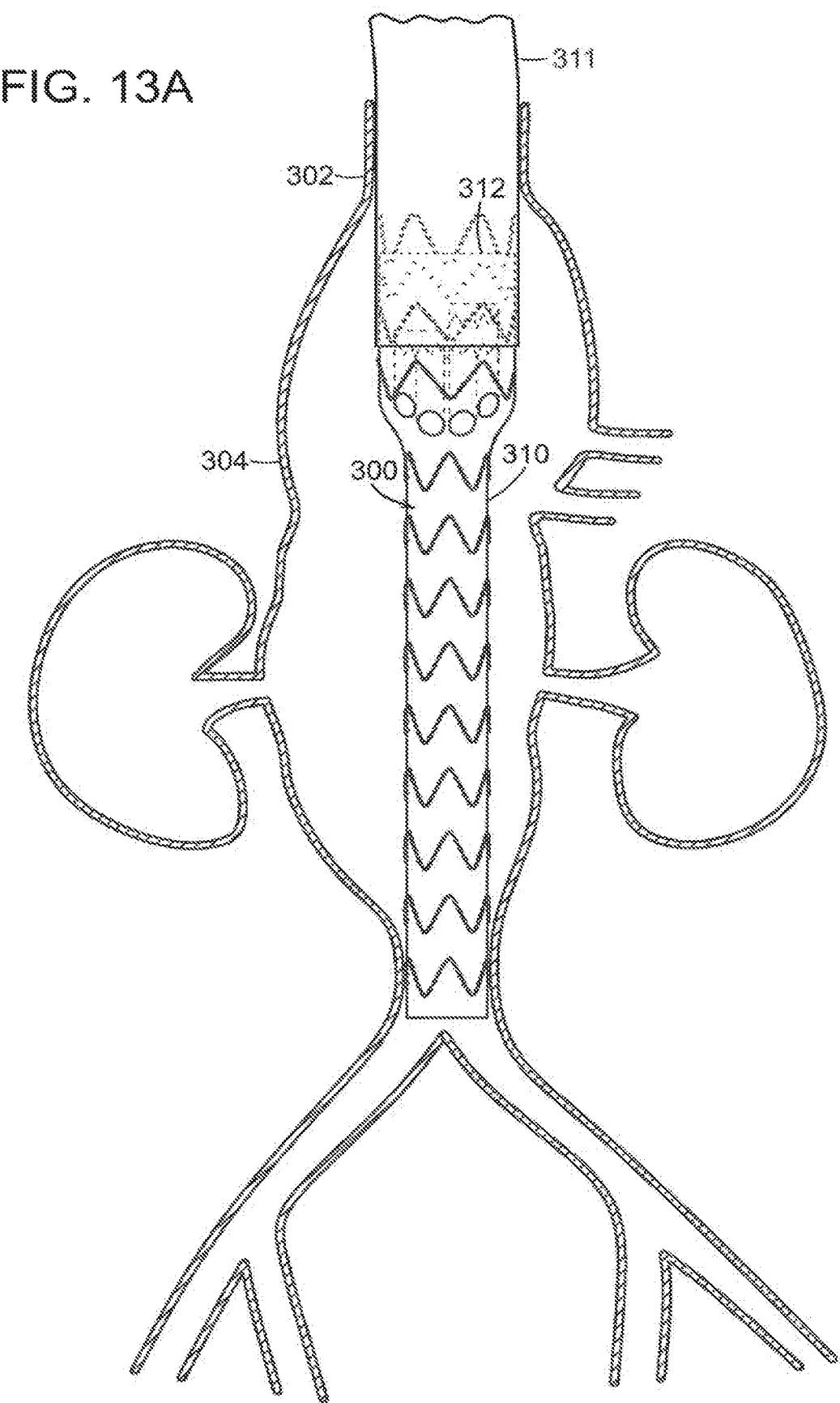
Figures 2, 13B:
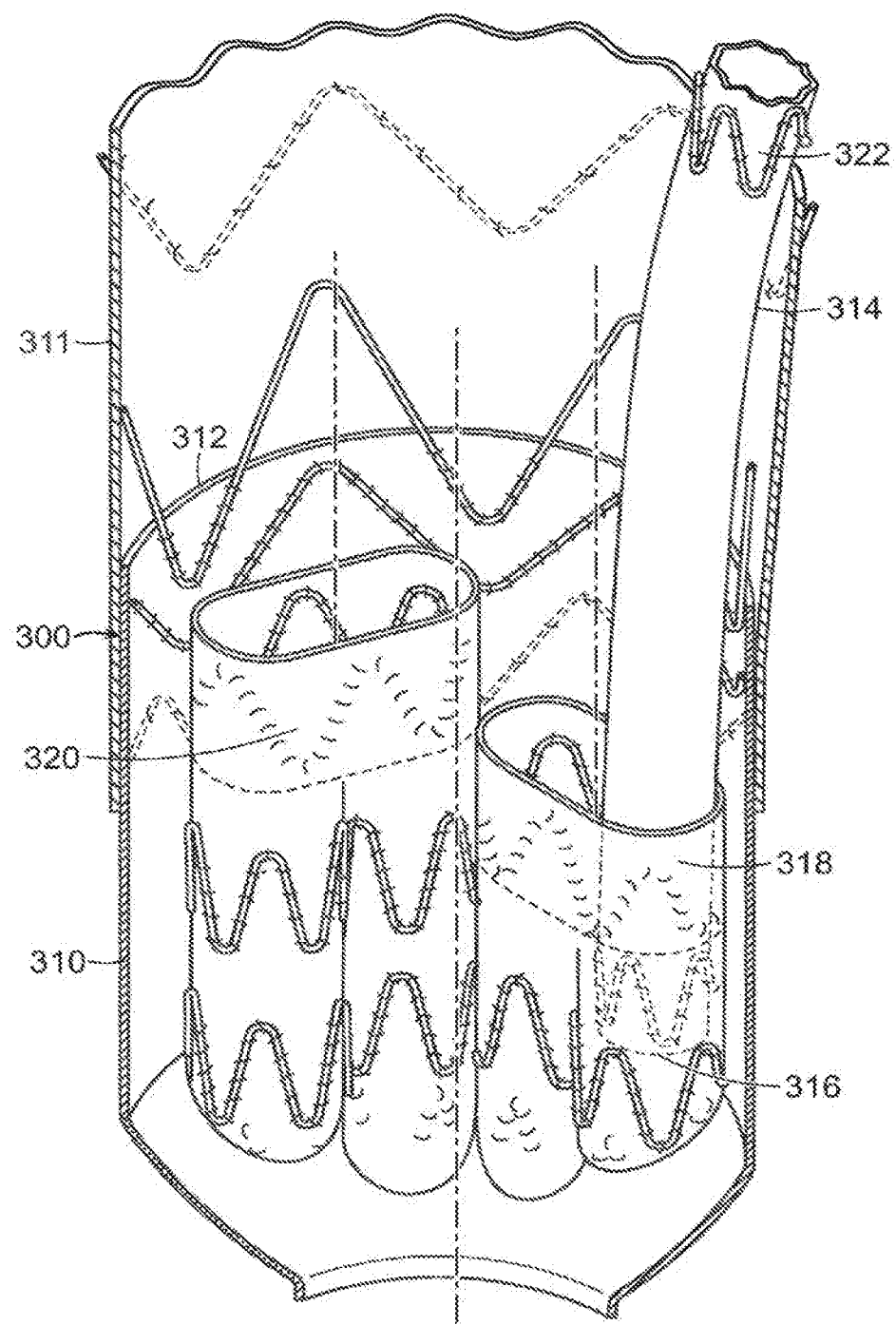
Figure 13C:
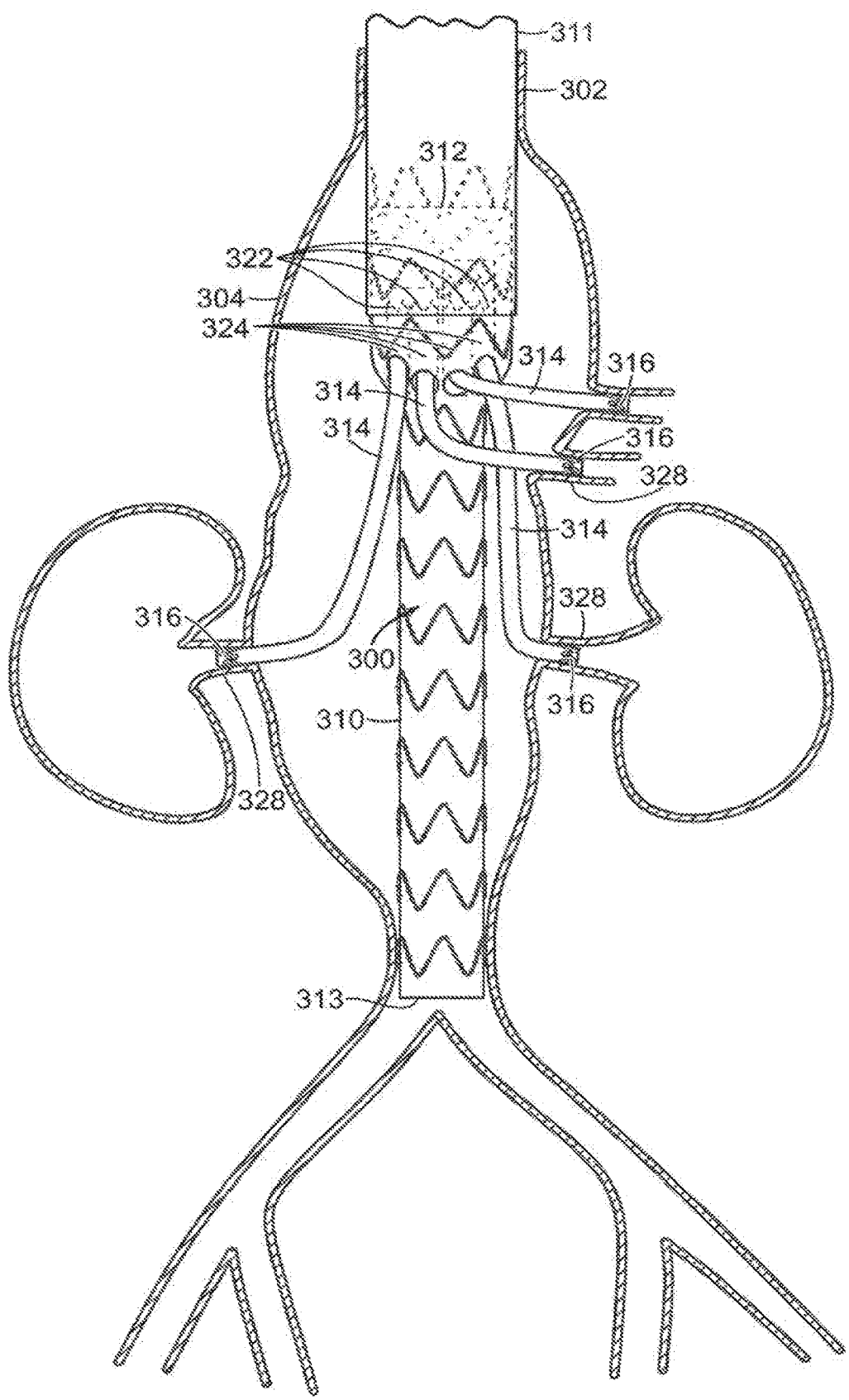

In a method of the invention, vascular repair device 300 of the invention is delivered through blood vessel 302 to an aneurysm site 304 of a patient, as shown in FIG. 13A. As can be seen in FIGS. 13B, 13B-1 and 13B-2, main prosthesis 310 includes proximal end 312 that is distal to proximal end 301 of aneurysm site 304 of the patient. Fenestrations 303,305 are proximal to fenestrations 307,309. Fenestrations 303,305,307 and 309 are all in fluid communication with sublumens defined by subprostheses within main prosthesis 310, as described with reference to embodiments described above. The stent at proximal open end 38 of main prosthesis 12 can include at least one active fixation component, such as a barb (not shown). In another embodiment, vascular repair device 10 employed in the methods of the invention can include crown stent 224 and clasping stent 232 at proximal open end 38 of main prosthesis 12 (not shown). Thoracic prosthesis 311 extends proximally from vascular repair device 10. Distal end 313 of main prosthesis 310 is distal to aneurysm 304. Additional vascular repair device 314 includes distal end 316, that is directed from a proximal direction into first internal lumen prosthesis 318 or second internal prosthesis 320 of vascular repair device 300. As shown in FIG. 13C, proximal end 322 of at least one additional vascular repair device 314 is inserted within sub-prosthesis 324 of main prosthesis 310 of vascular repair device 300. Distal ends 316 of vascular repair devices 314 are inserted into branch vessels 328 of blood vessel 302. Exemplary branch vessels include the celiac artery, superior mesenteric artery, left renal artery and right renal artery.

In an embodiment, shown in FIGS. 13A, 13B-1, 13B and 13C, at least one of the fenestrations is distal to at least one of another of the fenestrations at the midsection of the vascular repair device of the invention.

Figure 14:
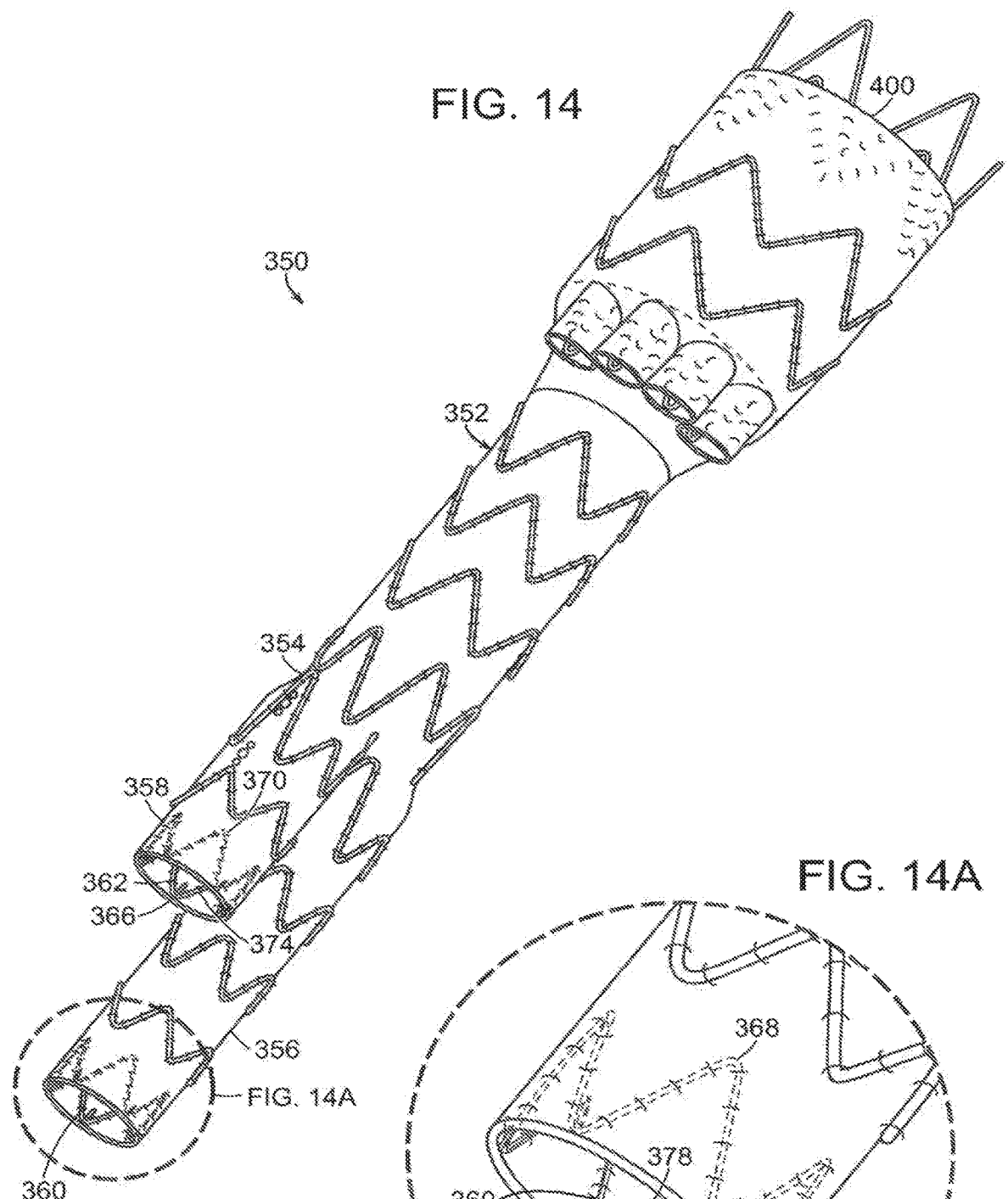
FIG. 14 is a perspective view of another embodiment of a vascular repair device of the invention where the distal end of the device is bifurcated.
Figure 14A:
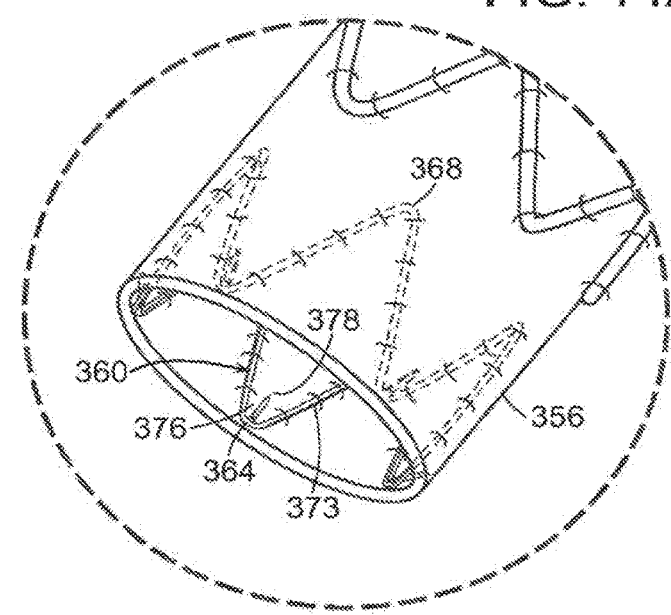
FIG. 14A is a detail of the perspective view into a distal open end of the embodiment of the vascular repair device of the invention taken from FIG. 14.

In another embodiment of the invention, shown in FIGS. 14 and 14A, vascular repair device 350 includes main prosthesis 352 and is bifurcated at distal end 354 of main prosthesis 352 to form legs 356,358, each of which includes at least one stent 360,362 with distal apices 364,366 and proximal apices 368,370 connected by struts 373,374, respectively. As described herein, bifurcated main prosthesis 352 can include at least one active fixation component. For example, as shown in FIG. 14A, stent 360 includes barb 378 extending proximally from distal apex 364.

Figure 15:
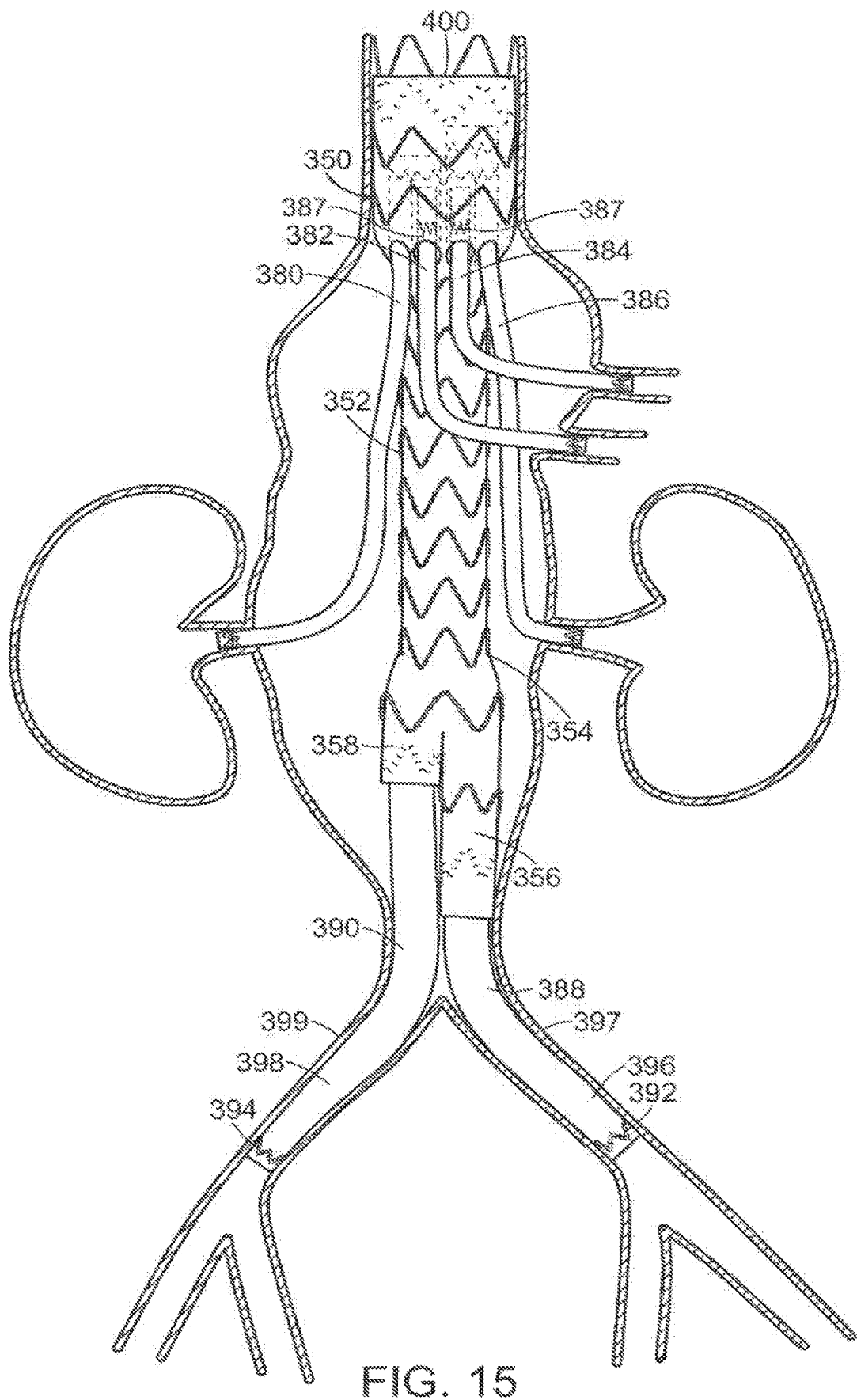
FIG. 15 represents placement of an embodiment of a vascular repair device of the invention shown in FIG. 14, including placement of additional vascular devices extending from the legs of the vascular repair device of the invention into the common iliac arteries of the patient into the aorta in an alternative method of the invention.

In one embodiment, vascular repair device 350 having distal end 354 of main prosthesis 352 that is bifurcated includes additional vascular repair devices 380,382,384 and 386, as shown in FIG. 15. In an embodiment, the additional vascular repair device includes an active fixation component 387 at the external surface of the proximal end of the graft component of the additional vascular repair device. As in the embodiment represented in FIGS. 13A-13C, additional vascular repair devices 380,382,384 and 386 include graft components, each having an external surface and an internal surface. Each graft component defines a lumen, a proximal open end, a distal open end and major longitudinal axis extending through the proximal and distal open ends and the lumen. The additional vascular prosthesis can include at least one stent having distal apices and proximal apices connected by struts, and each can include an active fixation component, as described above.

As also shown in FIG. 15, distal prostheses 388,390 extend from legs 356,358, respectively. Distal prostheses 388,390 include, as with additional vascular repair devices 380,382,384 and 386, stents 392,394 at their respective distal ends. Stents 392,394 can be located at an internal surface or an external surface of the respective distal prosthesis 388,390 and, if external, as shown in FIG. 15 can include an active fixation components, as described above. Distal prosthesis 388,390 are typically delivered into legs 356,358 from the distal end of each of legs 356,358. Alternatively, they can be delivered through proximal end 400 of vascular repair device 350. Distal ends 396,398 of distal prostheses 388,390 are fixed in a respective common iliac artery 397,399.

Figure 16:
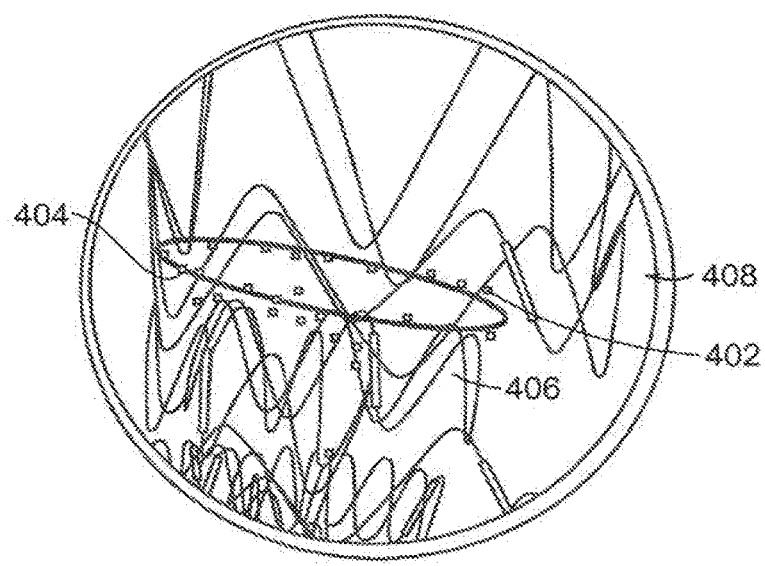
FIG. 16 represents locations of radiopaque markers on an embodiment of a vascular repair device of the invention.
Figure 17:
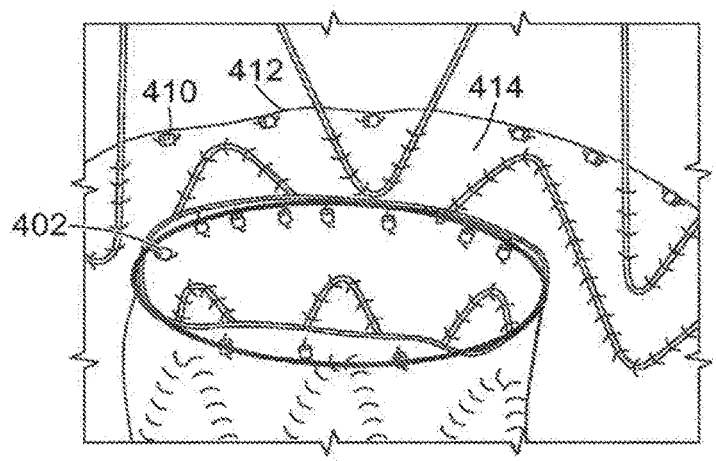
FIG. 17 represents locations of radiopaque markers on an embodiment of a vascular repair device of the invention.
Figure 18:
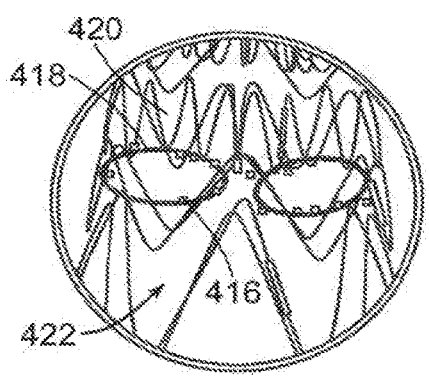
FIG. 18 represents locations of radiopaque markers on an embodiment of a vascular repair device of the invention.

Placement of vascular repair device can be aided by use of radiopaque markers 402, as is shown in FIGS. 16 through 18. As can be seen in FIG. 16, at least one radiopaque marker 402 is located at at least one proximal end 404 of at least one internal prosthesis 406 of vascular repair device 408. In another embodiment, shown in FIG. 17, at least one radiopaque marker 410 is located at proximal open end 412 of main prosthesis 414. In yet another embodiment, shown in FIG. 18, at least one radiopaque marker 416 is located at distal end 418 of sub-prosthesis 420 of vascular repair device 422. At least one radiopaque marker can be located at or proximate to at least one of proximal open end and distal open end of main prostheses 42.

Figure 19:
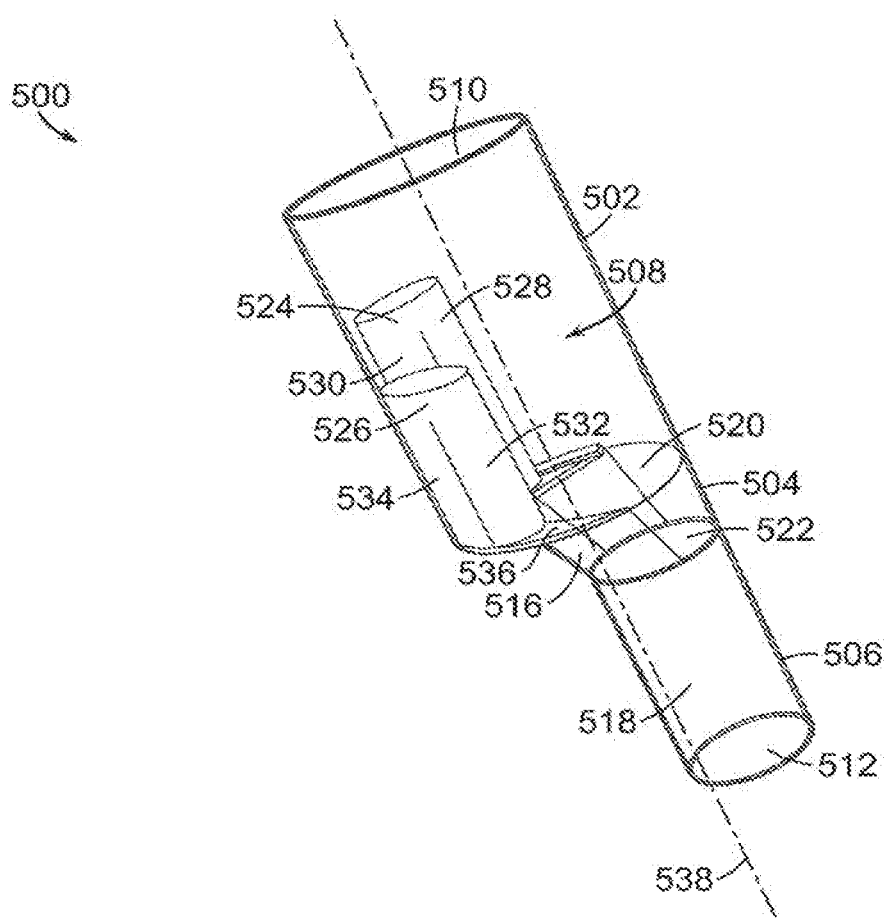
FIG. 19 is a wire drawing of one embodiment of a vascular repair device of the invention.
Figure 20:
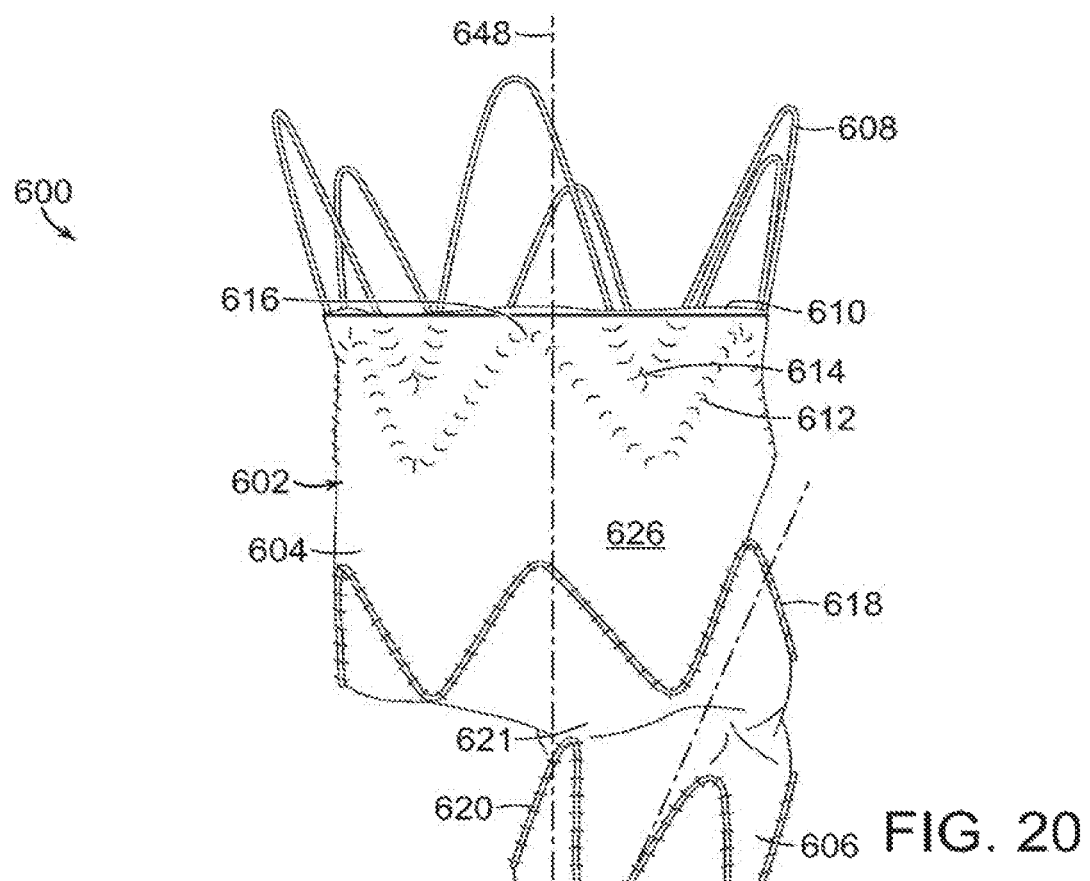
FIG. 20 is a side view of still another embodiment of a vascular repair of the invention.
Figure 21:
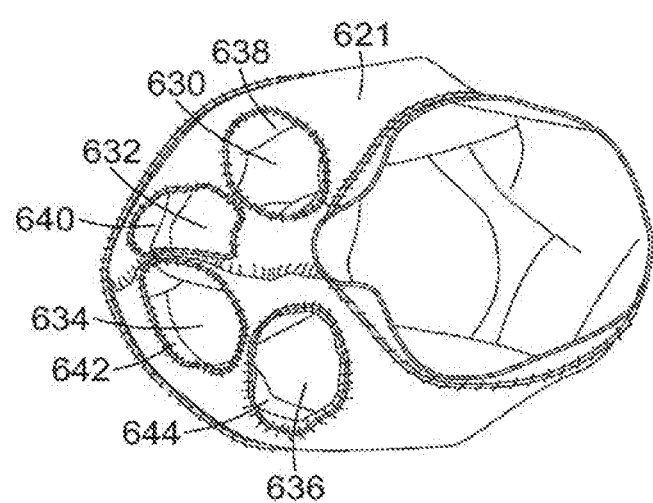
FIG. 21 is an end view of the vascular repair device shown in FIG. 20.

In another embodiment, graft component at midsection of main prosthesis narrows distally at an angle along first major longitudinal axis of main lumen as shown in FIGS. 19 through 21. In embodiments, the angle is at least one of about 5%, about 10%, about 15%, about 20%, about 25%, about 30%, about 35%, about 40%, about 45%, about 50%, about 55% and about 60%.

FIG. 19 is a wire drawing of another embodiment of the vascular repair device of the invention, shown in perspective. As shown therein, vascular repair device 500 includes proximal section 502, midsection 504 and distal section 506. Proximal section 502, midsection 504 and distal section 506 define main lumen 508. Vascular repair device 500 defines proximal opening 510 and distal opening 512. Main lumen 508 includes proximal lumen 514, midsection lumen 516 and distal lumen 518. Main lumen 508 is partitioned between proximal lumen 514 and midsection lumen 516 by proximal internal opening 520. Midsection lumen 516 and distal lumen 518 are partitioned by distal internal opening 522. First internal prostheses 524 and second internal prosthesis 526 are within proximal lumen 516. First internal subsection 528 and second internal subsection 530 extend distally from first internal prosthesis 524. Third internal subsection 532 and fourth internal subsection 534 extend distally from second internal prosthesis 526. Planar section 536 defines, in part, proximal internal lumen 520 and further defines distal openings of sub-prostheses 528,530,532,534. Midsection 504 tapers from proximal internal opening 520 to distal internal opening 522. Major longitudinal axis 538 extends through the center of proximal lumen 514.

FIG. 20 is a side view of yet another embodiment of the vascular repair device of the invention. Vascular repair device 600 includes main graft component 602 having proximal end 604 and distal end 606. Proximal stent 608 extends proximally from proximal end 604 and is secured to main graft component 602 at internal surface 610 of main graft component 602. Adjacent stent 612 is secured to internal surface 610 of the main graft component 602. Distal apices 614 of proximal stent 608 are nested between proximal apices 616 of adjacent stent 612. Stents 618,620 are on either side of transition section 621 between proximal end 604 and distal end 606 of vascular repair device 600 and are secured to external surface 626 of main graft component 602. As can be seen in FIG. 21, transition section 621 defines distal openings 630,632,634,636 of subsections 638,640, 642,644, respectively, within main graft component 602. Subsections 638,640,642,644, in turn, extend distally from internal prostheses (not shown) that are secured within main graft component 602. Referring back to FIG. 20, major longitudinal axis 648 of proximal end 604 is at a positive angle 652 to major longitudinal axis 650 of distal end 606 of vascular repair device 600

Suitable delivery systems for use in implanting vascular repair devices of the invention are described, for example, in the U.S. Pat. Nos. 8,292,943; 7,763,063; 8,308,790; 8,070, 790; 8,740,963; 8,007,605; 8,062,349, 8,062,345, 9,005, 264; 8,449,595; 8,636,788; 9,101,506 and U.S. application Ser. No. 13/310,987, the teachings of all of which are incorporated by reference in their entirety.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating aortic vascular damage, comprising the steps of:
    a) delivering a vascular repair device through a blood vessel to an aneurysm site of a patient, the vascular repair device including:
        i) a main prosthesis having a graft component that includes an external surface and an internal surface, the graft component including a proximal section, a midsection, a distal section, and a planar section between the proximal section and the midsection, the planar section defining openings, and wherein the proximal section defines a proximal open end, the midsection extends distally from a first of the openings of the planar section, and the distal section defines a distal open end, the proximal section defining a proximal lumen and a first major longitudinal axis extending through the center of the proximal lumen;
        ii) a first internal prosthesis within the proximal lumen, the first internal prosthesis having a graft component, an external surface and an internal surface, and defining at least in part a first internal lumen, a proximal end located distal to the proximal open end of the main prosthesis, a distal end and a longitudinal axis extending through the first internal lumen, the proximal end and the distal end, and being substantially parallel to the first major longitudinal axis;
        iii) a second internal prosthesis within the proximal lumen, the second internal prosthesis having a graft component, an external surface and an internal surface, and defining at least in part a second internal lumen, a proximal end located distal to the proximal end of the first internal prosthesis, a distal end and a longitudinal axis extending through the second internal lumen, the proximal end of the second internal prosthesis and the distal end of the second internal prosthesis, and being substantially parallel to the first major longitudinal axis, and wherein the first and second internal prostheses are on the same side of a plane bisecting the proximal lumen; and
        iv) two pairs of sub-prostheses, each of the sub-prostheses of the two pairs of sub-prostheses having a graft component defining a proximal end, a distal end, at least a portion of a sublumen and a longitudinal axis extending through the proximal end and the distal end of each of the respective sub-prostheses and through the sublumens of each of the respective sub-prostheses, the graft component of each of the sub-prostheses having an external surface and an internal surface, wherein a first pair of the sub-prostheses extends distally to a second and a third of the openings defined by the planar section, and the second pair of the subprostheses extends distally to a fourth and fifth of the openings defined by the planar section;
    b) directing at least one additional vascular repair device within one of the and second first internal lumen, the at least one additional vascular repair device including a graft component having an external surface and an internal surface;
    c) inserting the at least one additional vascular repair device within at least one of the two sub-prostheses of the main prosthesis of the vascular repair device; and
    d) inserting the distal end of the at least one additional vascular repair device into at least one branch vessel of the blood vessel, to thereby implant the prosthesis at the aneurysm site of the patient.

2. The method of claim 1, wherein the vascular repair device is delivered through the blood vessel to align the proximal open end of the main prosthesis cranial to the aneurysm site of the patient.

3. The method of claim 2, wherein the main prosthesis is bifurcated to form a first and a second bifurcated leg of the main prosthesis.

4. The method of claim 3, further including the steps of:
    a) directing a proximal end of at least one second additional vascular repair device into the distal end of at least one of the first and the second bifurcated leg of the main prosthesis, the at least one second additional vascular repair device including a graft component having an external surface and an internal surface;
    b) aligning the proximal end of the at least one second additional vascular repair device with the distal end of at least one of the first and the second bifurcated leg of the main prosthesis; and
    c) inserting the distal end of the at least one second additional vascular repair device into at least one additional branch vessel of the blood vessel, to thereby implant the prosthesis at the aneurysm site of the patient.

5. The method of claim 1, wherein the midsection narrows in a distal direction along the main lumen.

* * * * *